US010144720B2

(12) United States Patent
Davey et al.

(10) Patent No.: US 10,144,720 B2
(45) Date of Patent: Dec. 4, 2018

(54) PROCESS INVOLVING CROSS METATHESIS OF OLEFINS

(71) Applicant: Givaudan SA, Vernier (CH)

(72) Inventors: Paul Nicholas Davey, Duebendorf (CH); Martin Alan Lovchik, Duebendorf (CH); Andreas Goeke, Winterthur (CH); Krisztian Lorincz, Budapest (HU); Florian Toth, Magyarhertelend (HU); Levente Ondi, Veresegyhaz (HU)

(73) Assignee: GIVAUDAN S.A., Vernier (CH)

( * ) Notice: Subject to any disclaimer, the term of this patent is extended or adjusted under 35 U.S.C. 154(b) by 0 days.

(21) Appl. No.: 15/120,802

(22) PCT Filed: Mar. 13, 2015

(86) PCT No.: PCT/EP2015/055343
§ 371 (c)(1),
(2) Date: Aug. 23, 2016

(87) PCT Pub. No.: WO2015/136093
PCT Pub. Date: Sep. 17, 2015

(65) Prior Publication Data
US 2016/0368888 A1 Dec. 22, 2016

(30) Foreign Application Priority Data
Mar. 13, 2014 (GB) .................................. 1404468.9

(51) Int. Cl.
C07D 313/00 (2006.01)
C07C 67/343 (2006.01)
C07C 69/734 (2006.01)
C11B 9/00 (2006.01)

(52) U.S. Cl.
CPC .......... *C07D 313/00* (2013.01); *C07C 67/343* (2013.01); *C07C 69/734* (2013.01); *C11B 9/0084* (2013.01); *Y02P 20/582* (2015.11)

(58) Field of Classification Search
CPC ... C07D 313/00; C11B 9/0084; C07C 67/343; C07C 69/734; Y02P 20/582
USPC ....................................................... 549/266
See application file for complete search history.

(56) References Cited

U.S. PATENT DOCUMENTS

| 4,064,144 | A | 12/1977 | Tseng |
| 5,936,100 | A | 8/1999 | Fuerstner et al. |
| 6,255,276 | B1 * | 7/2001 | Frater .................. C07D 313/00 512/11 |
| 2011/0077421 | A1 * | 3/2011 | Schrock ............... B01J 31/1805 556/431 |

FOREIGN PATENT DOCUMENTS

| EP | 0908455 A1 | 4/1999 |
| JP | H1087526 | 4/1998 |
| WO | 9820119 A1 | 5/1998 |
| WO | 0136368 A2 | 5/2001 |
| WO | 2014018578 A1 | 1/2014 |

OTHER PUBLICATIONS

Villemin, A simple synthesis of trans-deta9-isoambrettolide, dihydroambrettolide, and methyl 16-acetoxy-9-hexadecenoate, Synthesis, 2, p. 154-155, 1 abstract page. (Year: 1987).*
International Search Report and Written Opinion of the International Searching Authority for corresponding application PCT/EP2015/055343 dated May 5, 2015.
GB Search report for corresponding application GB 1404468.9 dated Oct. 24, 2014.
R. R. Iyer, et al., "A convenient synthesis of n-triacontanol; a plant growth regulator", Chemistry & Industry, Society of Chemical Industry, London, England, Jan. 1986, pp. 398-399.
S. Chattopadhyay, et al., "A Convenient Synthesis of (Z)-9-Hexadecen-1-yl Acetate, a Sex Pheremone of Rice Green Catepillar, Naranga Aenescens, from Aleuritic Acid", Indian Journal of Chemistry, Section B, Counsel of Scientific and Industrial Research, IN, vol. 23, Mar. 1984, pp. 236-237.
A. S. Moriello, et al., "Development of the First Potential Covalent Inhibitors of Anandamide Cellular Uptake", Journal of the American Chemistry Society, US, vol. 49, No. 7, Jan. 2006, pp. 2330-2332.
G. B. V. Subramanian, et al. "Dilithium tetrachlorocuprate catalyzed alkylation of aleuritic acid derivatives and synthesis of muscalure", Indian Journal of Chemistry, Section B, Counsel of Scientific and Industrial Research, IN, vol. 35, Jul. 1996, pp. 724-726.
M. Hashimoto, et al., "Efficient synthesis of 3-trifluoromethylphenyldiazirinyl oleic acid derivatives and their biological activity for protein kinase C", Bioorganic & Medicinal Chemistry Letters, vol. 13, No. 9, May 2003, pp. 1531-1533.
P. Schweizer, et al., "Induction of resistance in barley against *Erysiphe graminis* f. sp. hordei by free cutin monomers", Physiological and Molecular Plant Pathology, vol. 49, No. 2, Aug. 1996, pp. 103-120.
M. Ukiya, et al., "Isolation, structural elucidation, and inhibitory effects if terpenoid and lipid constituents from sunflower pollen on Epstein-Barr virus early antigen induced by tumor promoter, TPA", Journal of Agricultural and Food Chemistry, American Chemistry Society, US, vol. 51, No. 10, May 2003, pp. 2949-2957.

(Continued)

*Primary Examiner* — Taylor V Oh
(74) *Attorney, Agent, or Firm* — Norris McLaughlin & Marcus PA

(57) ABSTRACT

A method of forming a macrocyclic musk compound comprising the steps of:—
i) cross-metathesizing a first olefin and a second olefin in the presence of a homogeneous transition metal catalyst comprising an alkylidene ligand, to form a statistical mixture of a hetero-dimer intermediate of said first and second terminal olefin, and homo-dimers
ii) separating the hetero-dimer from the statistical mixture of hetero- and homo-dimers
iii) and cyclizing the hetero-dimer intermediate to form the macrocyclic musk compound.

23 Claims, No Drawings

(56) References Cited

OTHER PUBLICATIONS

H. H. Mathur, et al., "Macrocyclic musk compounds. Part V. New Synthesis of exaltone, exaltolide, dihydroambrettolide, and ?9-isoambrettolide from aleuritic acid", Journal of the Chemical Society, Jan. 1963, pp. 3505-3509.

K. G. J. Nierop, et al., "Rapid molecular assessment of the bioturbation extent in sandy soil horizons under pine using ester-bound lipids by on-line thermally assisted hydrolysis and methylation-gas chromatography/mass spectrometry", Rapid Communications in Mass Spectrometry, vol. 18, No. 10, May 2004, pp. 1081-1088.

P. E Kolattukudy, et al.,"Structure and composition of aliphatic constituents of potato tuber skin (suberin)", Lipids, Springer-Verlag, Berlin/Heidelberg, vol. 9, No. 9, Sep. 1974, pp. 682-691.

B. F. Cravatt, et al., "Structure determination of an endogenous sleep-inducing lipid, cis-9-octadecenamide (oleamide): a synthetic approach to the chemical analysis of trace quantities of a natural product", Journal of the American Chemical Society, American Chemical Society, vol. 118, No. 3, Jan. 1996, pp. 580-590.

P.C. Mitter, et al., " Studies in long-chain acids. Part IV", J. Indian Chem. Soc., vol. 19, 1942, pp. 69-75.

J. Graca, et al., "Suberin structure in potato periderm: Glycerol, long-chain monomers, and glyceryl and feruloyl dimers", Journal of Agricultural and Food Chemistry, vol. 48, No. 11, Nov. 2000, pp. 5476-5483.

M. Prashad, et al., "Synthesis of 1-0-(15 carboxypentadecyl)-2-0-acetyl-sn-glycero-3-phosphorylcholine as a potential platelet activating factor (PAF) hapten", Chemistry and Physics of Lipids, Limerick, IR, vol. 53, No. 1, Mar. 1990, pp. 121-126.

J. Gebauer, et al., "Synthesis of [gamma], [delta]-unsaturated-[beta]-keto lactones via sequential cross metathesis-lactonization: A facile entry to macrolide antibiotic (-)-A26771B", The Journal of Organic Chemistry, vol. 71, No. 5, Mar. 2006, pp. 2021-2025.

R. Croteau, et al., "The constituent cutin acids of cranbury cuticle", Phytochemistry, Pergamon Press, GB, vol. 11, No. 1, Jan. 1972, pp. 353-363.

A. S. Williams, "The synthesis of macrocyclic musks", Synthesis, Georg Thieme Verlag, Stuttgart, DE, No. 10, Jan. 1999, pp. 1707-1723.

B. D. Mookherjee, et al., "Synthesis of -Isoambrettolide and its isomers from 1,9-cyclohexadecadiene", The Journal of Organic Chemistry, vol. 37, No. 24, 1972, pp. 3846-3848.

D. Villemin, et al., "Synthesis de Macrolides par Metathese", Tetrahedron Letters, vol. 21, pp. 1715-1718, 1980.

Chinese Office Action in corresponding application CN 201580013580.0 dated Aug. 8, 2018.

\* cited by examiner

PROCESS INVOLVING CROSS METATHESIS OF OLEFINS

This patent application claims the full priority benefit of PCT/EP2015/055343 filed 13 Mar. 2015, and to the earlier filed priority application, GB 1404468.9 filed 13 Mar. 2014. The entirety of the foregoing documents are herein incorporated by reference.

The present invention is concerned with a process for the preparation of macrocyclic musk compounds utilizing a cross metathesis reaction. The invention is also concerned with novel intermediates useful in said process of forming macrocyclic musk compounds.

The odour of musk is perhaps the most universally appreciated fragrance. Synthetic musks can be divided into three major classes—aromatic nitro musks, polycyclic musk compounds, and macrocyclic musk compounds. The detection of the nitro- and polycyclic chemical groups in human and environmental samples initiated a public debate on the use of these compounds. Some research has indicated that these musk compounds don't break down in the environment and can accumulate in human bodies. As such, macrocyclic musk compounds have increased in importance in recent years.

Common macrocyclic musk compounds include ambrettolide (9-ambrettolide and 7-ambrettolide), nirvanolide, habanolide, cosmone, muscenone, velvione, civetone and globanone.

7-Ambrettolide naturally occurs in musk ambrette seed oil (M. Kerschbaum, Chem Ber. 1927, 60B, 902) and is a valuable perfume base because of its desirable odour. 9-Ambrettolide is likewise a much appreciated perfumery ingredient (C. Collaud, Helv. Chim. Acta 1942, 25, 965). It is currently synthesized industrially from aleuritic acid. However, aleuritic acid is obtained from shellac by saponfication, and due to growing industrial concerns regarding the supply and price of shellac, there is a need to devise new synthetic routes into the highly valued and valuable 9-ambrettolide.

Olefin metathesis has become an important tool in the field of synthetic organic chemistry. A variant of olefin metathesis—so-called cross metathesis—is the reaction of two different olefins in the presence of an organometallic catalyst, in which one olefin double bond changes places with the other. More particularly, it is an organic reaction that entails the redistribution of fragments of olefins by the scission and regeneration of carbon-carbon double bonds.

The mechanism of this reaction is thought to proceed via a 2+2 cycloaddition of an alkene-bearing substrate to a metal alkylidene catalyst, forming a metallocyclobutane intermediate, which undergoes cycloreversion to generate the substrate loaded with a metal carbene, which further reacts with a second alkene to produce the metathesis product and releases the metal alkylidene catalyst.

Schematically, an olefin metathesis reaction can be represented as follows:

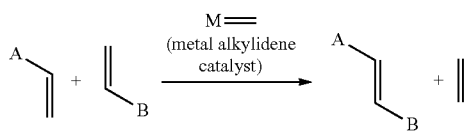

The reaction can be used to couple together two olefin substrates to form a new olefin compound, which is a dimer of the two substrates. The reaction is shown schematically, above. The A-containing substrate and the B-containing substrate can react to form a hetero-dimer (shown), however, the both the A-containing substrate and the B-containing substrate can react with itself to form homo-dimers.

Another variant of the olefin metathesis reaction is the so-called ring closure metathesis reaction (RCM). This reaction is widely established as a means of forming ring structures. The reverse reaction can be employed to ring-open a cyclic structure:

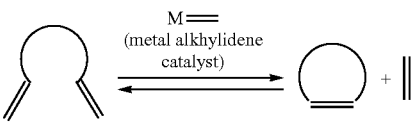

RCM is simply an intramolecular olefin metathesis of a diene, yielding a cycloalkene and a volatile alkene by-product (ethylene, in the case of the above schematic). RCM has been widely researched as a means of producing macrocycles. Indeed, a laboratory procedure utilizing a ring closure metathesis (RCM) reaction using a ruthenium alkylidene catalyst has been reported in the literature (J. Am. Chem. Soc. 2013, 135, 94; Chem. Europ. J. 2013, 19, 2726-2740, J. Org Chem. 1996, 61, 3942-3943, and WO 2012167171). However, a problem with RCM is that the intra-molecular ring closing reaction is in competition with inter-molecular polymerisation reactions, and the former is favoured only in high dilution, and so for reasons of economy this chemistry has not found use industrially as a means of producing macrocyclic musk compounds to the best of the applicant's knowledge.

In contrast to the greatly researched ring closure metathesis reaction, the cross metathesis reaction has been relatively under studied. Difficulties abound with this chemistry. Catalyst-induced migration of the double bonds on the starting materials represents a consistent challenge. Furthermore, differences in reactivity of the olefin groups of the starting materials can lead to poor yields of the desired product. Still further, the inevitable complex mixture containing homo-dimers and hetero-dimers can be difficult, time consuming and expensive to separate and isolate in pure form, particularly when the reaction and purification must be industrially scalable.

The present invention addresses the problems in the prior art and provides an efficient and high-yielding synthesis of macrocyclic musk compounds and their open-chain intermediates, utilizing cross metathesis.

Accordingly, the invention provides in a first aspect a method of forming a macrocyclic musk compound comprising the steps of cross metathesizing a first olefin and a second olefin in the presence of a homogeneous transition metal catalyst containing an alkylidene ligand, to form a hetero-dimer intermediate of said first and second olefin, and cyclizing the hetero-dimer intermediate to form the macrocyclic musk compound.

In a particular embodiment of the present invention, one or both of first and second olefins may be olefins with a terminal double bond.

In a particular embodiment of the invention, the first step in the preparation of the macrocyclic musk compound, wherein the first and second olefins are reacted in a cross metathesis reaction to produce the hetero-dimer intermediate is shown schematically below.

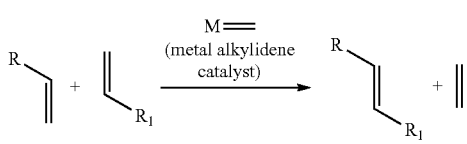

The group R contains a protected hydroxyl group containing 3 to 10 carbon atoms; $R_1$ is a carboxylic ester group containing 3 to 11 carbon atoms; wherein the number of carbon atoms in the ester group and protected hydroxyl group together should be less than 15; and wherein M=represents a transition metal catalyst containing an alkylidene ligand.

One of said first or second olefins may be represented by the formula (I)

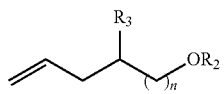

wherein $OR_2$ is a protected hydroxyl group, which may be selected from an alkyl ether group; an ester group; a silyl ether group; or a carbonate group; $R_3$ is H or methyl; and n is an integer from 1-8.

Suitable ether protecting groups include a branched or non-branched alkyl moiety containing 1 to 5 carbon atoms, for example methyl, ethyl, propyl, i-propyl, t-Bu or t-amyl.

Suitable ester protecting groups include $C(O)R_4$, wherein $R_4$=hydrogen, or a branched or non-branched alkyl moiety containing 1 to 7 carbon atoms, for example methyl, ethyl, propyl, i-propyl, t-butyl or t-amyl. Suitable silyl ether protecting groups include $Si(R_5)_3$; wherein $R_5$ is a branched or unbranched alkyl moiety, which may include methyl, ethyl and propyl and t-butyl.

Suitable carbonate protecting groups include $C(O)OR_6$, wherein $R_6$ is a branched or non-branched alkyl moiety, for example methyl, ethyl or propyl.

The other of said first or second olefins may be represented by the formula (II)

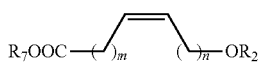

wherein $R_7$ is branched or non-branched alkyl moiety containing 1 to 5 carbon atoms, and preferably methyl or ethyl, and m is an integer from 1 to 10, preferably 7.

When first and second olefins specifically referred to above in formula (I) and (II) are subjected to a cross metathesis reaction in accordance with the present invention, the hetero-dimer intermediate can be represented by the formula (III)

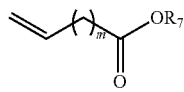

wherein $R_2$, $R_7$, m and n are as hereinabove defined, and wherein the configuration of the double bond may be E or Z as desired.

The hetero-dimer intermediates herein defined, as well as their preparation by cross metathesis each represent further aspects of the present invention.

In a particular embodiment of the present invention, the hetero-dimer intermediate is a compound represented by the formula (IV)

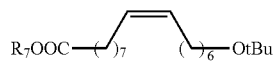

wherein $R_7$ is as hereinabove defined, in particular methyl.

The advantages of the t-Bu ether protecting group are manifold, and lead to an over-all efficiency of the synthesis of macrocyclic musks. In particular, the t-Bu protecting group is advantageous because it results in a hetero-dimer product that can be relatively easily separated from homo-dimer side products formed in the cross metathesis reaction by distillation at relatively low temperatures, e.g. below about 100 to 220 degrees centigrade at a pressure of about 1 to 10 mbar. Furthermore, this hetero-dimer is relatively easy to cleave under mild conditions during the subsequent macrocyclization step to form the macrocyclic musk.

After completion of the metathesis reaction, the hydroxyl protecting group can be cleaved by various synthetic procedures depending on the nature of the protecting group, all of which are well known to a person skilled in the art. The resultant α-ω hydroxy ester can be cyclized to form a macrocyclic lactone. In the particular case of a α-ω hydroxy esters represented in protected form (IV) above, the corresponding macrocyclic musk compound is the lactone E/Z 9-ambrettolide (structure shown below).

When the protecting group is an ester, the hetero-dimer formed by the metathesis reaction can be immediately submitted to the macrocyclization reaction without prior cleavage of the protecting group. Examples of the synthetic steps do not need to be exhaustively explained here, and are more specifically described in the examples, below.

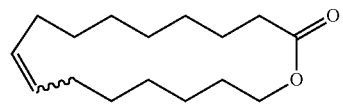 [SMILES: O=C1CCCCCCCC=CCCCCCCO1]

Thereafter, the macrocyclization reaction may be carried out according to techniques known in the art. A particular method of carrying out the cyclization step proceeds via the formation of a polyester from a hydroxy ester, which is the unprotected hetero-dimer of the metathesis reaction, and continuously trans-esterifying the polyester into volatile lactones and removing them at higher temperature and reduced pressure once the lactone is formed according to the well-known Collaud chemistry disclosed U.S. Pat. No. 2,234,551, which is herein incorporated by reference. Further details regarding this chemistry are set forth in the examples hereinbelow.

Whereas a hetero-dimer intermediate described above can be cyclized to form 9-ambrettolide, the skilled person will appreciate that with the appropriate selection of olefin starting materials, in particular unsaturated protected alcohol and unsaturated carboxylic acid ester, the cross metathesis reaction will form hetero-dimers that can be subsequently transformed by macrocyclization to form other macrocyclic musk compounds such as 7-Ambrettolide

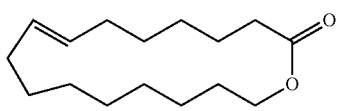 [SMILES: O=C1CCCCC/C=C/CCCCCCCCO1]

or Habanolide

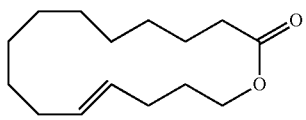 [SMILES: O=C1CCCCCCCCC/C=C/CCCO1]

or Nirvanolide

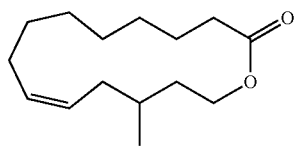 [SMILES: CC1C/C=C\CCCCCCCC(=O)OCC1]

For example, the first and second olefin compounds that can be used to form 7-ambrettolide may be selected from 10-(tert-butoxy)dec-1-ene and methyl oct-7-enoate or dec-9-en-1-yl acetate and methyl oct-7-enoate.

The first and second olefin compounds that can be used to form Habanolide may be selected from trimethyl(pent-4-en-1-yloxy)silane and ethyl dodec-11-enoate.

The first and second olefin compounds that can be used to form Nirvanolide may be selected from 4-methyl-6-(tert-butoxy)hex-1-ene and methyl 9-decenoate, or 4-methyl-6-(tert-butoxy)hex-1-ene and ethyl 9-decenoate, or 3-methyl-hex-5-en-1-yl propionate and methyl 9-decenoate.

The cross metathesis reaction conditions required to conjoin the two olefins are generally well known in the art. The reaction may proceed at room temperature or at elevated or lowered temperatures, for example between 0 to 60 degrees centigrade.

Whereas in ring closure metathesis reactions to form macrocycles, it is necessary to carry out the reaction in very high dilutions (for example, $10^{-2}$ to $10^{-4}$ M solutions), in contrast applicant has found that in the present invention the cross metathesis reaction will proceed at high concentrations, and indeed the reaction may even be carried out with no solvent present. As such, the method of the present invention, whereby a hetero-dimer is first formed by metathesis, and then ring-closed by a macrocyclization step, represents a considerably simpler and cheaper process than RCM to form macrocyclic musk compounds, which is industrially scalable in an economic manner.

Elimination of solvent from a reaction mixture has very obvious economic advantages for the industrialization of a synthetic procedure. An additional advantage related to the reduction or avoidance of a solvent, particularly in relation to the use of metathesis catalysts that may be water and oxygen sensitive, is that there is one less reagent that needs to be conditioned or purified before use to eliminate trace contaminants such as moisture and reactive oxygen, such as in the form of peroxides.

In a particular aspect of the present invention, feed stock containing first or second olefin compounds can be subjected to a purification step prior to their reaction by cross metathesis. Purification entails the removal of contaminants from said feed stocks containing the olefin compounds that could otherwise negatively affect the reactivity of metathesis catalysts. Such contaminants may include water, alcohols, aldehydes, peroxides, hydroperoxides, protic materials, polar materials, Lewis base (basic) catalyst poisons and two or more thereof. Purification may entail a physical purification step, for example, a distillation step, or a step whereby the olefin compounds are separated from unwanted contaminants by a process of absorption. Physical purification means may include heat (such as, in a distillation process), or contact of the feed stocks with absorbent materials selected from molecular sieves, alumina, silica gel, montmorillonite clay, Fuller's earth, bleaching clay, diatomaceous earth, zeolites, kaolin, activated metals, metal sulfates, metal halides, metal silicates, activated carbon, and soda ash.

Additionally or alternatively, purification may entail a chemical purification step, whereby unwanted contaminants are separated from the feed stocks by subjecting the contaminants to a chemical reaction, whereby they are converted to materials that are non-reactive with a metathesis catalyst. Chemical purification means include treating the feed stocks with metal carbonates and metal hydrogen carbonates, acid anhydrides, metal hydrides, phosphorous pentoxide, metal aluminum hydrides, alkyl aluminum hydrides, trialkyl aluminums, metal borohydrides, organometallic reagents, metal amides, and combinations thereof. Contaminants may be compounds that contain at least one proton that can react with a compound selected from the group consisting of metal carbonates and metal hydrogen carbonates, acid anhydrides, metal hydrides, phosphorous pentoxide, metal aluminum hydrides, alkyl aluminum hydrides, trialkyl aluminums, metal borohydrides, organometallic reagents, metal amides, and combinations thereof.

Purification may also be performed by contacting feed stock with materials selected from the group consisting of molecular sieves, activated alumina, activated acidic alumina, neutral alumina, any one of which may be optionally heat treated; and activated basic alumina, alkaline earth metal hydrides, alkaline earth metal sulfates, alkali metal sulfates, alkali earth metal halides, alkali metal aluminum hydrides, alkali metal borohydrides, Grignard reagents; organolithium reagents, trialkyl aluminums, metal bis(trimethylsilyl)amides, and combinations thereof.

Purification may also be performed by contacting feed stock with $CaH_2$, activated Cu, activated Mg, acetic anhydride, calcium sulfate, magnesium sulfate, potassium sulfate, aluminum sulfate, potassium magnesium sulfate, sodium sulfate, calcium carbonate, sodium carbonate, magnesium silicate, potassium chloride, $LiAlH_4$, $NaAlH_4$, $iBu_2AlH$, n-butyl lithium, t-butyl lithium, sec-butyl lithium, triethyl aluminum, tributyl aluminum, triisopropyl aluminum, trioctyl aluminum, lithium diisopropyl amide, KHMDS, and combinations thereof.

Purification may also be carried out by subjecting feed stock to an anhydride of an organic acid. Suitable anhydrides are preferably the anhydrides of aliphatic, cyclic, alicyclic organic acids having from 1 to 10 carbon atoms, or an aromatic organic acid having from 6 to 10 carbon atoms. Such compounds are known in the art or may be produced according to known methods. A particularly useful organic anhydride is acetic anhydride.

Purification may also be carried out by subjecting feed stock to an organometallic compound of aluminum. Said organometallic compound of aluminum may be a tri-substituted aluminium compound wherein the substituents are independently selected from an aliphatic, cyclic, alicyclic residue having from 1 to 10 carbon atoms, or from aromatic residues having from 6 to 10 carbon atoms. Such compounds are known in the art or may be produced according to known methods.

In one embodiment, the organometallic compound of aluminum is triethyl aluminum, tributyl aluminum, triisobutyl aluminum, triisopropyl aluminum, or trioctyl aluminum.

Trioctyl aluminum is particularly preferred since it is stable in contact with air, i.e. is not-flammable in contact with air, which is not the case with triethyl aluminum. This renders it particularly suitable for applications at an industrial scale.

For the practical realization of a chemical purification step, the amount of contaminant may be determined by known methods, such as chromatographic methods. Thereafter, the theoretical amount of purification means needed to react with the contaminant and render it inactive to a catalyst can be easily calculated, and can be employed in slight molar excess in order to ensure that all potentially harmful contaminant is reacted to render it inactive towards a catalyst. If desired, after the reaction with contaminant, any excess purification means can be removed.

After purification, feedstock containing first and/or second olefin compounds useful in the present invention may have a level of purity that is at least 99.9% by weight of the first and/or the second olefin, or at least 99.99% by weight, or at least 99.999% by weight.

Several different and complementary means of purification of a contaminated feedstock comprising said first and/or said second olefin compounds can be carried out prior to a metathesis reaction according to the invention. The following non-exhaustive and non-limiting list of representative purification methodologies can be usefully employed, for example (a) thermal treatment—for example, heating (and/or distilling) a feed stock at a temperature of between about 100° C. and about 250° C., depending on the boiling point of a feed stock, optionally with a purge of an inert gas or under vacuum, and/or treatment with an adsorbent material referred to hereinabove can be useful both in decomposing peroxide contaminants and/or decomposition products thereof or adsorbing contaminants; (b) treatment with an acid anhydride (e.g., acetic anhydride, $Ac_2O$) can be useful in removing moisture, active hydroxyl-containing materials (e.g., alcohols), and hydroperoxides (via acetylation); (c) treatment with a desiccant (e.g., silica gel, alumina, molecular sieves, magnesium sulfate, calcium sulfate, and the like, and combinations thereof) and/or an organometallic reagent (e.g., t-butyl lithium, triethyl aluminum, tributyl aluminum, triisobutyl aluminum, triisopropyl aluminum, trioctyl aluminum, and the like, and combinations thereof) and/or metal hydrides (e.g., $CaH_2$ and the like) and/or acid anhydrides (e.g., acetic anhydride and the like) can be useful in removing moisture; (d) treatment with an adsorbent (e.g., alumina, silica gel, and the like, and combinations thereof) and/or an organometallic reagent (e.g., t-butyl lithium, triethyl aluminum, tributyl aluminum, triisobutyl aluminum, triisopropyl aluminum, trioctyl aluminum, and the like, and combinations thereof) and/or a metal amide (e.g., LDA, KHMDA, and the like) can be useful in removing protic materials; (e) treatment with an adsorbent (e.g., alumina, silica gel, activated charcoal, and the like, and combinations thereof) can be useful in removing polar materials; and (f) treatment with an organometallic reagent (e.g., t-butyl lithium, triethyl aluminum, tributyl aluminum, triisobutyl aluminum, triisopropyl aluminum, trioctyl aluminum, and the like, and combinations thereof) can be useful in removing Lewis basic catalyst poisons or the like.

In some embodiments, the means used to purify said feedstock prior to a metathesis reaction comprises an adsorbent which, may be selected from the group consisting of silica gel, alumina, bleaching clay, activated carbon, molecular sieves, zeolites, Fuller's earth, diatomaceous earth, and the like, and combinations thereof. In some embodiments, the means is selected from the group consisting of optionally heat-treated molecular sieves, optionally heat-treated alumina, and a combination thereof. In some embodiments, the adsorbent comprises optionally heat-treated activated alumina which, may be selected from the group consisting of optionally heat-treated activated acidic alumina, optionally heat-treated activated neutral alumina, optionally heat-treated activated basic alumina, and combinations thereof. In some embodiments, the absorbent comprises optionally heat-treated activated neutral alumina, which can be useful in treating substrates (e.g., olefins) that are susceptible to acid-catalyzed isomerization and/or rearrangement.

For embodiments in which the means for purification comprises an adsorbent (e.g., molecular sieves, alumina, etc.), it is presently believed that the treating of the feedstock with the adsorbent is more effectively performed by flowing the feedstock through the means for purification using a percolation- or flow-type system (e.g., chromatography column) as opposed to simply adding the adsorbent to the substrate in a container. In some embodiments, about 20 wt % of alumina is used in a column. In particular, it may be particularly advantageous to treat a feedstock with alumina on about a 5-to-1 weight-to-weight basis. However, it is to be understood that the amount of alumina used is not restricted and will be both feedstock- and impurity dependent in addition to being impacted by the form of the alumina, its activation process, and the precise treatment method (e.g., flow through a column vs. direct addition to container). In some embodiments, the means used for purifying the feedstock prior to a metathesis reaction comprises a trialkyl aluminum which, in some embodiments, is selected from the group consisting of triethyl aluminum, tributyl aluminum, triisobutyl aluminum, triisopropyl aluminum, trioctyl aluminum, and the like, and combinations thereof.

It has further been unexpectedly found that the purification period of the feed stock may significantly influence efficacy of the chemical purification step. Accordingly, prolonged purification periods may improve catalytic activity of the compounds used as catalysts in the metathesis reactions according to the invention.

In one embodiment, preferably when a trialkyl aluminum compound is used for purification, preferably trioctyl aluminum, the feedstock is subjected to said compound for a period of from 2 to 100 h, preferably 5 to 90 h, more preferred 10 to 80 h, and still more preferred 15 to 70 h.

Catalysts for effecting metathesis reactions are well known in the art. Generally, olefin metathesis catalysts are organometallic catalysts bearing a transition metal atom, such as titanium (Ti), tantalum (Ta), ruthenium (Ru), molybdenum (Mo) or tungsten (W). Whilst varying considerably in terms of the ligands bound to the metal atom, all of the effective catalyst systems share the basic metal alkylidene or alkylidyne ligand structure. Reviews of metathesis catalysts useful in the present invention are described in Michrowska et al Pure Appl. Chem., vol 80, No. 1, pp 31-43 2008; Schrock et al Chem. Rev. 2009, 109, 3211-3226; and Grubbs et al J. Am. Chem. Soc. 2011, 133, 7490-7496. Suitable catalysts are also described in the patent literature, for example in US 2013/0281706 and U.S. Pat. No. 6,306,988.

The variety of substituents or ligands that can be employed in the catalysts means that there are, today, a wide variety of catalysts available. Ligands or substituents may be selected to affect catalyst stability or selectivity (chemo-, regio- and enantio-selectivity), as well as turn over number (TON), and turn over frequency (TOF). As is well known in the art, the TON describes the degree of activity of a catalyst, i.e. the average number of substrate molecules converted per molecule of catalyst, whereas TOF is a representation of catalyst efficiency (in units 0).

Particularly useful catalysts in the metathesis reaction of the present invention are those metal alkylidene catalysts wherein the metal atom is either a Ruthenium, Molybdenum or Tungsten atom. Most preferred are said catalysts wherein the metal atom is Molybdenum or Tungsten.

Preferred Molybdenum or Tungsten catalysts are represented by the general formula

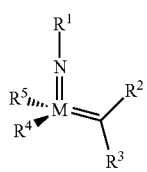

wherein

M=Mo or W; $R^1$ is aryl, heteroaryl, alkyl, or heteroalkyl; optionally substituted; $R^2$ and $R^3$ can be the same or different and are hydrogen, alkyl, alkenyl, heteroalkyl, heteroalkenyl, aryl, or heteroaryl; which are optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X=O and $R^6$ is aryl, which are optionally substituted; or X=S and $R^6$ is aryl, which are optionally substituted; or X=O and $R^6$ is ($R^7$, $R^8$, $R^9$)Si; wherein $R^7$, $R^8$, $R^9$ are alkyl or phenyl, which are optionally substituted; or X=O and $R^6$ is ($R^{10}$, $R^{11}$, $R^{12}$)C, wherein $R^{10}$, $R^{11}$, $R^{12}$ are independently selected from phenyl, alkyl; which are optionally substituted;

or $R^4$ and $R^5$ are linked together and are bound to M via oxygen, respectively Particularly preferred metathesis catalysts are set forth below.

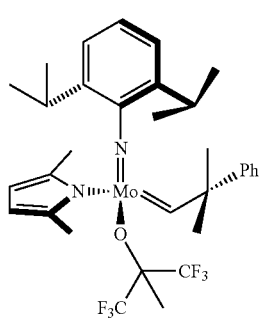

X001

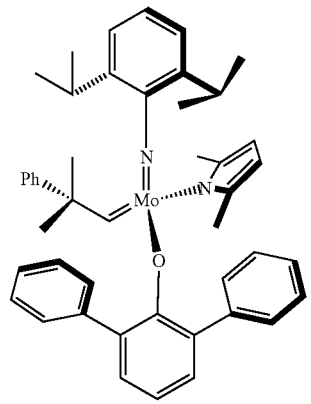

X004

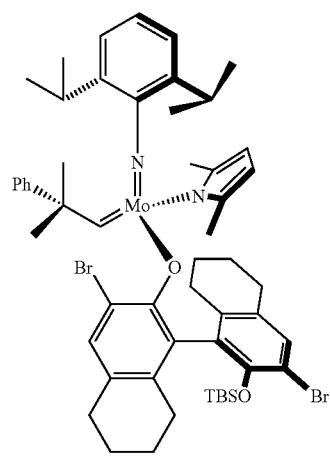

X007

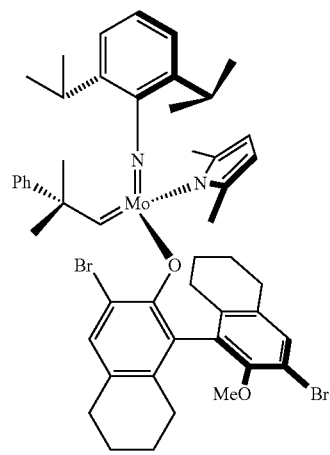

X008

-continued
X030
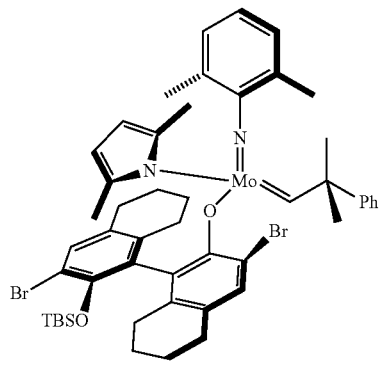
X038
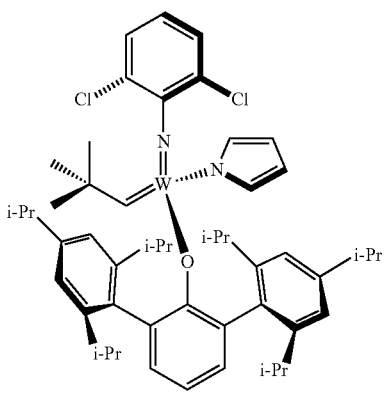
X039
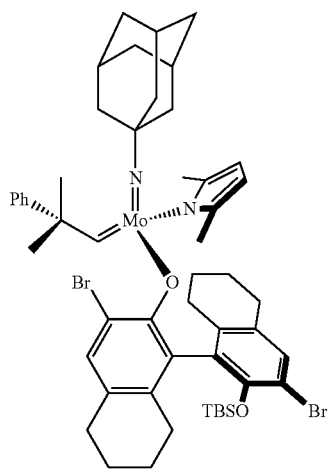
X040
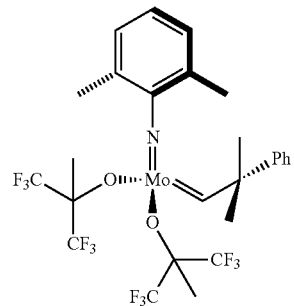
-continued
X041
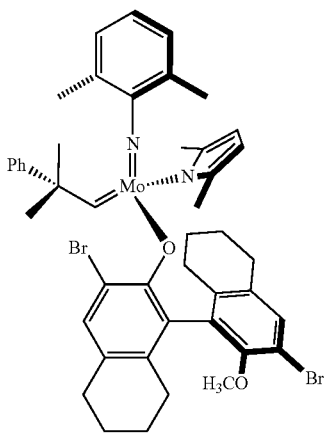
X042
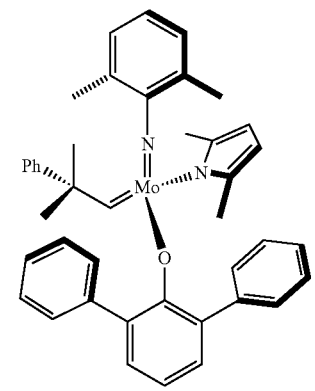
X046
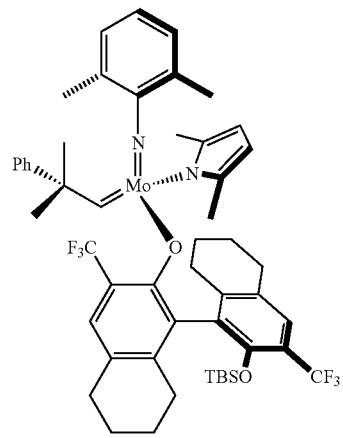
X051
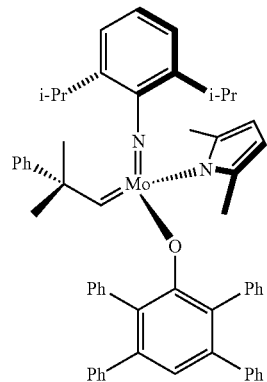

X052 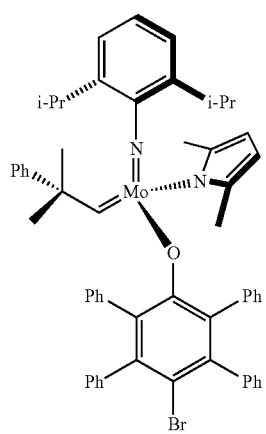
X054 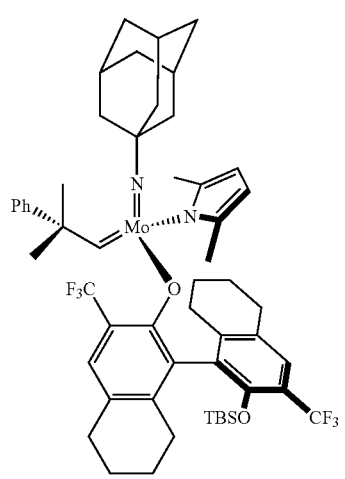
X059 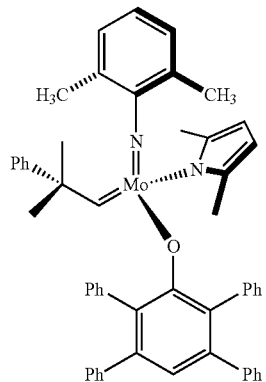
X061 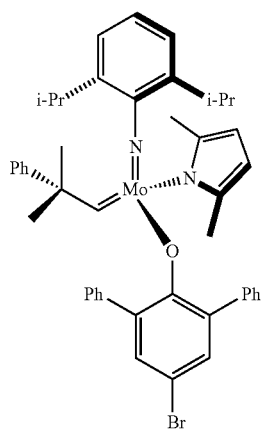
X062 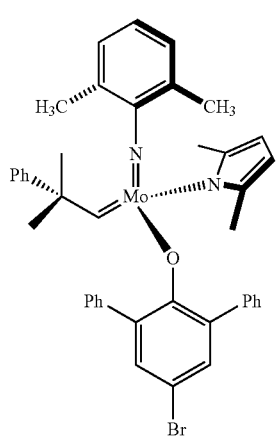
X063 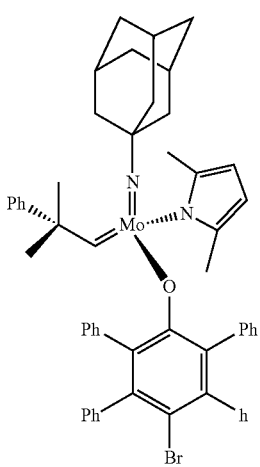

X076

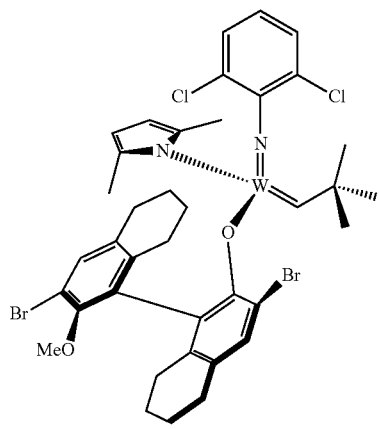

X114

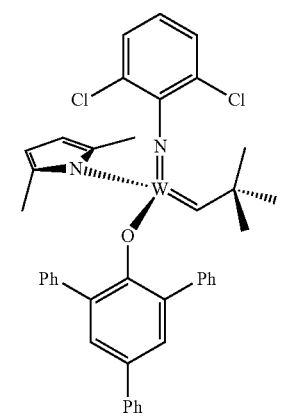

X123

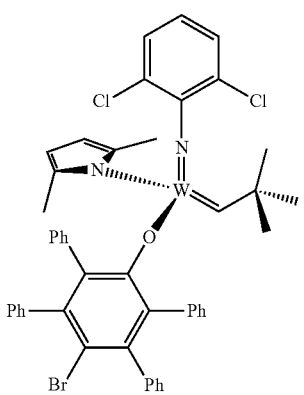

X149

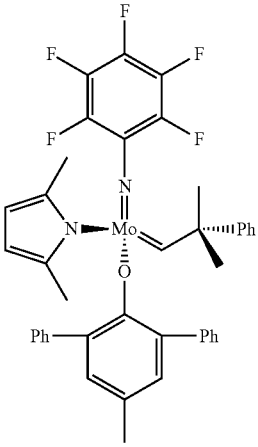

X154

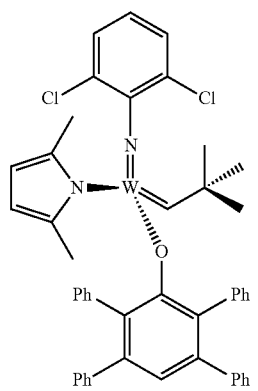

X190

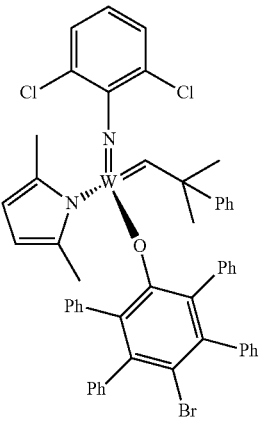

The selection of the catalyst may have significant effects on both the efficiency of the metathesis reaction, characterized by the catalyst loading in ppm, as well as on the diastereoselectivity, i.e. the E/Z ratio of the double bond in the macrocyclic ring. For instance, catalysts X052, X061, X123 and X190 are preferred catalysts for the synthesis of E9-Ambrettolide. These catalysts generally generate high E-selectivities and high conversions. Catalysts X039 and X054, which are characterized by particularly large phenolic ligands, are capable of producing high Z-selectivities in the cross metathesis reaction and are the preferred catalysts for the synthesis of Nirvanolide. The selection of optimized conditions of the cross-metathesis reaction depends on the nature of the individual substrate, the catalyst and its loadings as well as the degree of purification of substrates and solvents (if used), as further described in detail below.

The olefins used as substrates in the metathesis reaction of the present invention may be employed in a molar ratio of 1:X, wherein X is 1 or greater, and may be an integer or a number having a fractional part. More particularly, X is an integer or a number having a fractional part, between 1 and 10.

Assuming full conversion, statistically, a 1:1 mixture of olefin substrates will result in a maximum yield of 50% of the desired hetero-dimer product and 25% each of two homo-dimer products. Whereas, at first sight this appears to represent only a moderate yield of the desired hetero-dimer product, it represents a thermodynamic mixture and is the highest yield of hetero-dimer that can be achieved. If X is an integer or a number having a fractional part, which is greater than 1, then a mixture of hetero-dimer to first and second homo-dimers will be obtained in a molar ratio of $2X:1:X^2$.

Employing a ratio of 1:X, wherein X is a relatively large number would make economic sense if the first homo-dimer (the minor reaction product in the mixture) was a dimer of relatively expensive olefin starting material, and the second homo-dimer (the overwhelmingly major product in the reaction mixture) was the homo-dimer of a relatively inexpensive olefin starting material, or was otherwise an industrially useful by-product in its own right, or was easily and cheaply separable from the other ingredients of the mixture, for example, by re-crystallization.

Irrespective of the molar ratio of olefin starting materials that is employed in the present invention, the result of the metathesis reaction is a complex mixture. In order for such a reaction to be industrially scalable, it should be possible to separate the desired hetero-dimer from the homo-dimers in a cheap and efficient manner. Applicant has surprisingly found that the judicious selection of the protecting group for the hydroxyl group on the olefin starting material of formula (I) above can influence the down-stream purification of the hetero-dimer. More particularly, when the protecting group is an alkyl ether, and more particularly the iso-propyl or t-butyl ether, not only is there is clear separation of the boiling points of the hetero-dimer and the homo-dimers, but all of the dimers in the reaction mixture boil at relatively low temperatures, such that distillation can be employed at relatively low temperatures, e.g. about 100 to 220 degrees centigrade, at easily attainable reduced pressure of about 1 to 10 mbar. Furthermore, the t-butyl protecting group is easily cleavable, which provides that the subsequent macrocyclization step to form the macrocyclic musk can be carried out under relatively mild reaction conditions.

Accordingly, in another aspect of the present invention, the mixture of the hetero-dimer and homo-dimers formed by the cross-metathesis reaction may be separated by distillation, wherein the distillation temperature is between 100 to 220 degrees centigrade at a pressure of between 1 to 10 mbar.

In a particular embodiment of the present invention, in the method of separating the mixture of hetero-dimer from the homo-dimers, the mixture is formed from a first and second olefin employed in a 1:1 molar ratio.

In a particular embodiment of the present invention, in a method of separating the mixture of hetero-dimer from the homo-dimers, the protecting group on the hetero-dimer is an alkyl ether, and more particularly a t-butyl ether.

In order for a process to be industrially scalable, not only must it be possible to easily and cheaply separate the hetero-dimer from the homo-dimers, it should also be possible to recycle the homo-dimer by-products. The homo-dimer by-products can be treated with ethylene and a metathesis catalyst to regenerate the first and second olefin starting materials in a straightforward manner and conventional manner.

Accordingly, in another aspect of the present invention, the homo-dimers formed in a cross-metathesis reaction described herein, are separated from the hetero-dimer, and are treated with ethylene to regenerate first and second olefins.

The ethylenolysis treatment of the homo-dimers can be carried out under an appropriate pressure of ethylene gas. An appropriate pressure of ethylene would be between 1 bar and 20 bar. The reaction may be carried out at a temperature of between 10° C. and 50° C.

Whereas ethylenolysis is an efficient way to re-cycle the homo-dimers, nevertheless, one has to work under a high pressure of ethylene, which adds complexity and cost to the process.

Surprisingly, applicant has found that rather than subjecting the homo-dimers to ethylenolysis to regenerate the first and second olefins, the homo-dimers can be directly re-cycled by adding to them an amount of metathesis catalyst and subjecting them to a metathesis reaction.

In this re-cycling step, the homo-dimers may be mixed together as the sole reactants in a cross-metathesis reaction; or they may singularly, or in combination, be admixed with one or both of first and second olefins, before subjecting this mixture in a cross-metathesis reaction. Different recycling scenarios are schematically presented below. For example, the homo-dimers can be re-cycled alone, as set out in Scenario 1 below, or they can be re-cycled in admixture with first and second olefins (Scenario 2); or one homo-dimer can be reacted with the complementary olefin (Scenario 3 or 4).

The skilled person will appreciate that the homo-dimers can be mixed, optionally with the first and second olefins, to form a a statistical mixture in which the desired hetero-dimer 16ai is again formed with 50% yield. In this way, after a second metathesis step the hetero-dimer can be converted with 75% yield.

Accordingly, in another aspect of the present invention, the cross-metathesis reaction comprises a cross-metathesis step of first and second olefins defined hereinabove, and a subsequent cross-metathesis step of homo-dimers formed from the preceding cross-metathesis step.

The skilled person will appreciate that the recycling of homo-dimers is not limited to single recycling step. Subsequent recycling steps can be carried out, all of which can achieve a statistical mixture containing the desired hetero-dimer with 50% yield. Of course, the absolute amount of hetero-dimer recovered after each recycling step diminishes and so the number of recycling steps one performs is determined by the diminishing economic returns.

Scenario 1:

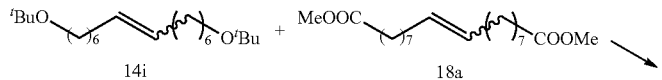

19

-continued

Scenario 2:

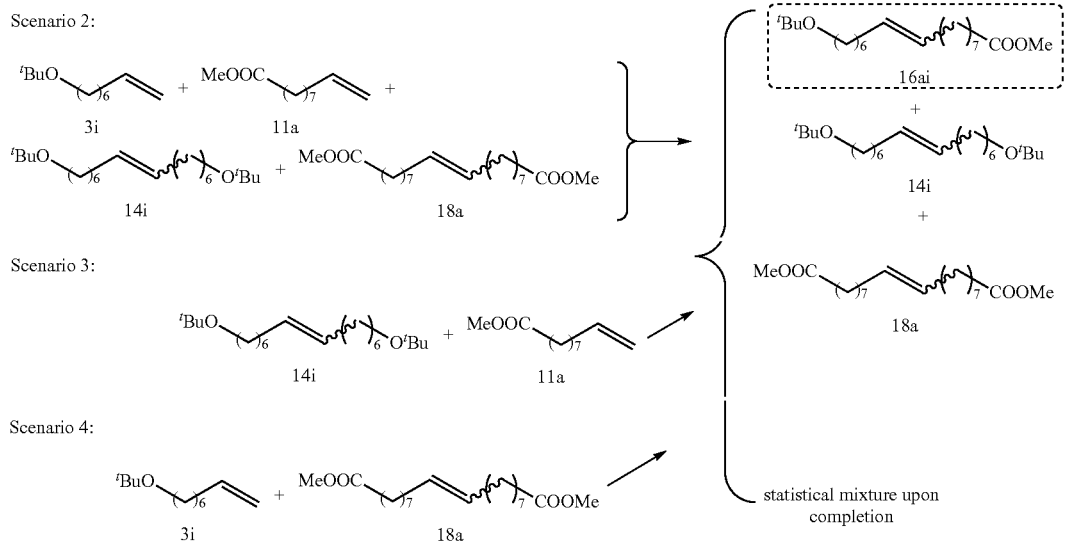

Scenario 3:

Scenario 4:

The fact that homo-dimers could be re-cycled in this way was surprising. The homo-dimers contain internal double bonds and as such would be expected to react very slowly, if at all, and it was not predictable that a statistical mixture containing the desired hetero-dimer would be formed, at least in a reasonable time that would make sense in the context of an industrial process. However, applicant found that the homo-dimers displayed substantially similar reaction kinetics as the first and second olefins, even when the first and second olefins contained terminal double bonds.

The synthetic methods described herein are particularly atom efficient, and as such represent a very efficient means of producing macrocyclic musk compounds on an industrial scale.

In particular, the use of terminal olefins as starting materials means that ethylene is eliminated as a by-product of the metathesis reaction. Only two carbon atoms are lost in this case, and if desired, the generated ethylene can be recovered and used in any subsequent ethyleneolysis reaction that is carried out on the homo-dimers.

However, notwithstanding the advantages attendant to the use of terminal olefins, applicant found that there are drawbacks associated with their use. In particular, the elimination of ethylene as a by-product can reduce the efficiency of the metathesis catalysts. Without wishing to be bound by any particular theory, it is possible that ethylene could deactivate the catalysts to a certain extent. Still further, certain metathesis catalysts, and in particular the ruthenium-based catalysts, can cause the terminal double bond of each of the starting materials to migrate, and also cause isomerization on the double bond in the hetero-dimer.

Surprisingly, however, applicant found that when using molybdenum and tungsten metathesis catalysts, and particularly those preferred molybdenum and tungsten catalysts referred to specifically hereinabove, there was substantially no double bond migration. Furthermore, there was relatively little isomerization about the double bond of the hetero-dimer. For example, with regard to the molecule 9-Ambrettolide, it was possible to obtain the molecule with high E-specificity. More particularly, it was possible to obtain E/Z 9-Ambrettolide in a ratio of about 80:20 to 90:10, more particularly about 85:15.

There now follows a series of examples, which serves to illustrate the invention.

SYNTHESIS OF OLEFIN SUBSTRATES

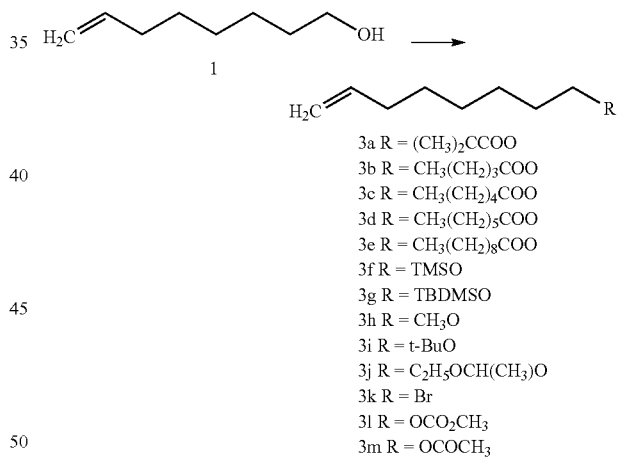

Scheme 1. Synthesis of oct-7-enol derivatives.

3a R = $(CH_3)_3CCOO$
3b R = $CH_3(CH_2)_3COO$
3c R = $CH_3(CH_2)_4COO$
3d R = $CH_3(CH_2)_5COO$
3e R = $CH_3(CH_2)_8COO$
3f R = TMSO
3g R = TBDMSO
3h R = $CH_3O$
3i R = t-BuO
3j R = $C_2H_5OCH(CH_3)O$
3k R = Br
3l R = $OCO_2CH_3$
3m R = $OCOCH_3$

Oct-7-en-1-yl 2,2-dimethylpropanoate (3a)

oct-7-en-1-ol (1) (50.00 g, 390 mmol) and triethylamine (43.4 g, 429 mmol, 59.8 mL, 1.1 equiv.) were dissolved in dry dichloromethane (500 mL) and 1.1 equivalent of pivaloyl chloride (2) (51.7 g, 429 mmol, 52.80 mL) was added dropwise to the reaction mixture and it was stirred at rt overnight. After the reaction had been completed, it was washed with water (3×100 mL) and brine (2×100 mL), dried over magnesium sulphate and evaporated. The crude product was purified by distillation (80-82° C./5 Hg mm) to yield 24.26 g (29.30%) ester (3a) as a colorless liquid. $^1$H-NMR (200 MHz, $CDCl_3$): δ 1.19 (s, 9H), 1.28-1.42 (m, 6H), 1.54-1.68 (m, 2H), 2.04 (q, J=7.0 Hz, 2H), 4.04 (t, J=7.0 Hz, 2H), 4.90-5.06 (m, 2H), 5.68-5.90 (m, 1H). GC-MS: 96.2% MS (EI): 212.

Oct-7-en-1-yl pentanoate (3b)

2.0 equivalents of thionyl chloride (23.29 g, 195.8 mmol, 14.22 mL) were added to a solution of valeric acid (4) (10.00 g, 97.9 mmol) in dry dichloromethane (100 mL) and the reaction mixture was stirred at rt for 6 h. After completion of the reaction, it was concentrated, then the residue was dissolved in dry dichloromethane (100 mL), cooled to 5-10° C. and 1.3 equivalent of oct-7-en-1-ol (1) (16.32 g, 127 mmol) was added to the reaction mixture in one portion followed by dropwise addition of triethylamine (12.88 g, 127 mmol, 17.74 mL, 1.3 equiv.) and stirred at rt for 3 h. After the reaction had been completed, it was washed with water (3×50 mL) and brine (2×50 mL), dried over magnesium sulphate and evaporated. The crude product was purified by distillation (94-97° C./7 Hg mm) to yield 13.20 g (63.50%) ester (3b) as a colorless liquid. $^1$H-NMR (200 MHz, CDCl$_3$): δ 0.91 (t, J=7.0 Hz, 3H), 1.24-1.46 (m, 8H), 1.54-1.70 (m, 4H), 2.04 (q, J=7.0 Hz, 2H), 2.29 (t, J=7.0 Hz, 2H), 4.05 (t, J=7.0 Hz, 2H), 4.88-5.06 (m, 2H), 5.69-5.91 (m, 1H). GC-MS: 96.4% MS (EI): 212.

Oct-7-en-1-yl hexanoate (3c)

2.0 equivalents of thionyl chloride (20.49 g, 172.2 mmol, 12.51 mL) were added to a solution of hexanoic acid (5) (10.00 g, 86.1 mmol) in dry dichloromethane (100 mL) and the reaction mixture was stirred at rt for 6 h. After completion of the reaction, it was concentrated, then the residue was dissolved in dry dichloromethane (100 mL) cooled to 5-10° C. and 1.3 equivalent of oct-7-en-1-ol (1) (14.35 g, 112 mmol) was added to the reaction mixture in one portion followed by dropwise addition of triethylamine (11.33 g, 112 mmol, 15.60 mL, 1.3 equiv.) and stirred at rt for 3 h. After the reaction was completed, it was washed with water (3×50 mL) and brine (2×50 mL), dried over magnesium sulphate and evaporated. The crude product was purified by distillation (96-98° C./7 Hg mm) to yield 14.15 g (72.6%) ester (3c) as a colorless liquid. $^1$H-NMR (200 MHz, CDCl$_3$): δ 0.89 (t, J=7.0 Hz, 3H), 1.21-1.45 (m, 10H), 1.54-1.70 (m, 4H), 2.04 (q, J=7.0 Hz, 2H), 2.28 (t, J=7.0 Hz, 2H), 4.05 (t, J=7.0 Hz, 2H), 4.88-5.04 (m, 2H), 5.68-5.90 (m, 1H). GC-MS: 95.8% MS (EI): 226.

Oct-7-en-1-yl heptanoate (3d)

2.0 equivalents of thionyl chloride (18.27 g, 153.6 mmol, 11.12 mL) were added to a solution of heptanoic acid (6) (10.00 g, 76.8 mmol) in dry dichloromethane (100 mL) and the reaction mixture was stirred at rt for 6 h. After completion of the reaction, it was concentrated, then the residue was dissolved in dry dichloromethane (100 mL) cooled to 5-10° C. and 1.3 equivalent of oct-7-en-1-ol (1) (12.80 g, 99.8 mmol) was added to the reaction mixture in one portion followed by dropwise addition of triethylamine (10.10 g, 99.8 mmol, 13.92 mL, 1.3 equiv.) and stirred at rt for 3 h. After the reaction had been completed, it was washed with water (3×50 mL) and brine (2×50 mL), dried over magnesium sulphate and evaporated. The crude product was purified by distillation (97-99° C./7 Hg mm) to yield 13.56 g (73.40%) ester (3d) as a colorless liquid. $^1$H-NMR (200 MHz, CDCl$_3$): δ 0.88 (t, J=7.0 Hz, 3H), 1.20-1.41 (m, 12H), 1.54-1.70 (m, 4H), 2.04 (q, J=7.0 Hz, 2H), 2.28 (t, J=7.0 Hz, 2H), 4.05 (t, J=7.0 Hz, 2H), 4.88-5.06 (m, 2H), 5.68-5.90 (m, 1H). GC-MS: 95.2% MS (EI): 240.

Oct-7-en-1-yl decanoate (3e)

2.0 equivalents of thionyl chloride (20.73 g, 174.2 mmol, 12.65 mL) were added to a solution of decanoic acid (7) (15.00 g, 87.1 mmol) in dry dichloromethane (150 mL) and the reaction mixture was stirred at rt for 6 h. After completion of the reaction, it was concentrated then the residue was dissolved in dry dichloromethane (150 mL) cooled to 5-10° C. and 1.3 equivalent of oct-7-en-1-ol (1) (14.52 g, 113 mmol) was added to the reaction mixture in one portion followed by dropwise addition of triethylamine (11.46 g, 113 mmol, 15.78 mL, 1.3 equiv.) and stirred at rt for 3 h. After the reaction had been completed, it was washed with water (3×70 mL) and brine (2×70 mL) dried over magnesium sulphate and evaporated. The crude product was purified by distillation (146-148° C./5 Hg mm) to yield 16.85 g (68.50%) ester (3e) as a colorless liquid. $^1$H-NMR (200 MHz, CDCl$_3$): δ 0.87 (t, J=7.0 Hz, 3H), 1.16-1.46 (m, 18H), 1.52-1.72 (m, 4H), 1.92-2.10 (m, 2H), 2.28 (t, J=7.0 Hz, 2H), 4.05 (t, J=7.0 Hz, 2H), 4.88-5.08 (m, 2H), 5.68-5.90 (m, 1H). GC-MS: 95.6% MS (EI): 282.

Trimethyl(oct-7-en-1-yloxy)silane (3f)

A solution of chlorotrimethylsilane (8) (50.84 g, 468 mmol, 1.2 equiv.) in dry dichloromethane (150 mL) was added to a solution of oct-7-en-1-ol (1) (50.00 g, 390 mmol) and imidazole (31.86 g, 468 mmol) in dry dichloromethane (350 mL) and the reaction mixture was stirred at 40° C. overnight. After the reaction had been completed, it was washed with water (3×100 mL) and brine (2×100 mL), dried over magnesium sulphate and evaporated. The crude product was purified by distillation (76-80° C./5 Hg mm) to yield 64.22 g (82.20%) silyl ether (3f) as a colorless liquid. $^1$H-NMR (200 MHz, CDCl$_3$): δ 0.10 (s, 9H), 1.24-1.60 (m, 8H), 2.04 (q, J=7.0 Hz, 2H), 3.56 (t, J=7.0 Hz, 2H), 4.88-5.06 (m, 2H), 5.70-5.92 (m, 1H). GC-MS: >99.0% MS (EI): 200.

tert-Butyldimethyl(oct-7-en-1-yloxy)silane (3g)

A solution of tert-butylchlorodimethylsilane (9) (64.70 g, 429 mmol, 1.1 equiv.) in dry dichloromethane (150 mL) was added to a solution of oct-7-en-1-ol (1) (50.00 g, 390 mmol) and imidazole (31.90 g, 468 mmol, 1.2 equiv.) in dry dichloromethane (350 mL) and the reaction mixture was stirred at rt overnight. After the reaction had been completed, it was washed with water (3×100 mL) and brine (2×100 mL), dried over magnesium sulphate and evaporated. The crude product was purified by distillation (85-90° C./5 Hg mm) to yield 52.20 g (55.20%) silyl ether (3g) as a colorless liquid. $^1$H-NMR (200 MHz, CDCl$_3$): δ 0.05 (s, 6H), 0.89 (s, 9H), 1.28-1.42 (m, 6H), 1.42-1.58 (m, 2H), 2.04 (q, J=7.0 Hz, 2H), 3.60 (t, J=7.0 Hz, 2H), 4.90-5.06 (m, 2H), 5.70-5.90 (m, 1H). GC-MS: 98.1% MS (EI): 242.

8-Methoxyoct-1-ene (3h)

Under inert atmosphere sodium hydride (20.60 g, 858 mmol, 2.2 equiv.) was suspended in dry THF (300 mL) and a solution of oct-7-en-1-ol (1) (50.00 g, 390 mmol) was added dropwise to the suspension over a 20-minute period, then it was stirred at rt for 30 min. After completion of the salt formation, iodomethane (66.4 g, 468 mmol, 1.2 equivalent) was added to the reaction mixture and it was stirred at rt overnight. After completion of the reaction the reaction mixture was concentrated to ⅓ and the residue was dissolved in chloroform (500 mL). The organic phase was washed with water (3×100 mL) and brine (2×100 mL), dried over magnesium sulphate and evaporated. The crude product was purified by distillation (65-70° C./25 Hg mm) to yield 26.50 g (47.80%) methyl ether (3h) as a colorless liquid. $^1$H-NMR (200 MHz, CDCl$_3$): δ 1.24-1.44 (m, 6H), 1.46-1.60 (m, 2H), 2.04 (q, J=7.0 Hz, 2H), 3.28 (s, 3H), 3.45 (t, J=7.0 Hz, 2H), 4.90-5.08 (m, 2H), 5.70-5.90 (m, 1H). GC-MS: 96.3% MS (EI): 142.

8-(tert-Butoxy)oct-1-ene (3i)

Ca. 3.0 equiv. of isobutylene was bubbled into the solution of oct-7-en-1-ol (1) (150.0 g, 176.0 mL, 1170 mmol) and 0.2 equiv. of sulphuric acid (23.90 g, 13.0 mL) in tert-butyl methyl ether (400 mL) at −20-−10° C. (ca. 25-35 min), then it was allowed to warm up to room temperature and stirred for 24 h. After completion of the reaction (TLC: Hep:EtOAc=7:3) the excess of isobutylene was removed in vacuum (500 Hgmm), then the reaction mixture was diluted with sat. Na$_2$CO$_3$ (the pH was adjusted to 7.5-8.5), the phases were separated, the aqueous phase was extracted with tert-butyl methyl ether (2×150 mL). Combined organic phases were washed with water (3×150 mL), brine (3×150 mL), dried over CaCl$_2$ (min. 8-12 h) and evaporated. The crude product was purified by vacuum distillation (69-74° C./8 Hg mm) to yield 153.00 g (71.10%) 3i as a colorless liquid. $^1$H-NMR (200 MHz, CDCl$_3$): δ 1.18 (s, 9H), 1.26-1.42 (m, 6H), 1.44-1.58 (m, 2H), 2.03 (q, J=7.0 Hz, 2H), 3.32 (t, J=7.0 Hz, 2H), 4.87-5.06 (m, 2H), 5.70-5.92 (m, 1H). GC-MS: 98.0% MS (EI): 184.

1-Ethoxy-1-(oct-7-en-1-yloxy)ethane (3j)

A catalytic amount of trifluoroacetic acid (0.178 g, 1.56 mmol, 0.005 equivalent) was added to the solution of oct-7-en-1-ol (1) (40.00 g, 312 mmol) and ethyl vinyl ether (10) (67.50 g, 936 mmol, 3.0 equivalent) at 0-5° C., then the reaction mixture allowed to warm up to rt and stirred for 2 h. After completion of the reaction, it was diluted with ether (500 mL) and washed with saturated aqueous solution of NaHCO$_3$ (3×100 mL), water (2×100 mL) and brine (2×100 mL), dried over magnesium sulphate and evaporated. The crude product was purified by distillation (82-84° C./6 Hg mm) to yield 36.54 g (58.50%) 3j as a colorless liquid. $^1$H-NMR (200 MHz, CDCl$_3$): δ 1.21-1.65 (m, 14H), 2.03 (q, J=7.0 Hz, 2H), 3.35 (t, J=7.0 Hz, 2H), 3.61 (q, J=7.0 Hz, 3H), 4.71 (q, 1=7.0 Hz, 1H), 4.92-5.10 (m, 2H), 5.68-5.91 (m, 1H). GC-MS: 96.9% MS (EI): 200.

8-Bromooct-1-ene (3k)

Phosphorus tribromide (27.21 g, 97.5 mmol, 0.5 equiv.) was added dropwise to a solution of oct-7-en-1-ol (1) (25.00 g, 195 mmol) in dry dichloromethane (200 mL) at 0° C. After completion of the addition it was allowed to warm up to rt and stirred for 2 h, then the reaction mixture was poured into saturated aqueous solution of NaHCO$_3$ to adjust the pH to 7.0. Phases were separated and the organic phase was washed with water (3×75 mL), brine (3×75 mL), dried over magnesium sulphate and evaporated. The crude product was purified by vacuum distillation (59-61° C./7 Hg mm) to yield 6.20 g (16.60%) 3k as a colorless liquid. $^1$H-NMR (200 MHz, CDCl$_3$): δ 1.20-1.50 (m, 6H), 1.76-1.92 (m, 2H), 1.96-2.14 (m, 2H), 3.14 (t, J=7.0 Hz, 2H), 4.90-5.08 (m, 2H), 5.70-5.92 (m, 1H). GC-MS: 96.8% MS (EI): 190, 192.

Methyl oct-7-enyl carbonate (3l)

Under inert atmosphere a 2.5M solution of butyllithium (93.6 mmol, 25.95 g, 37.4 mL) was added dropwise to a solution of oct-7-en-1-ol (1) (10.00 g, 78 mmol) in dry THF (100 mL) at 0° C. then it was stirred at the same temperature for 30 min. After completion of the salt formation, methyl chloroformate (8.85 g, 93.6 mmol, 7.23 mL) was added to the reaction mixture and it was stirred at rt overnight. After completion of the reaction the reaction mixture it was quenched with saturated aqueous solution of ammonium chloride and it was extracted with dichloromethane (3×100 mL). The organic phase was washed with water (2×50 mL) and brine (50 mL), dried over magnesium sulphate and evaporated. The crude product was purified by distillation (105-107° C./20 Hgmm) to yield 7.72 g (53.10%) carbonate (3l) as a colorless liquid. $^1$H-NMR (300 MHz, CDCl$_3$): δ 1.21-1.48 (m, 6H), 1.55-1.70 (m, 2H), 1.95-2.05 (m, 2H), 3.78 (s, 3H), 3.88 (t, J=7.1 Hz, 2H), 4.90-5.06 (m, 2H), 5.70-5.90 (m, 1H). GC-MS: 97.2% MS (EI):

187. Methyl dec-9-enoate (11a)

Decenoic acid (12) (32.60 g, 192 mmol) was dissolved in dry methanol (300 mL) and 0.1 equiv. of sulfuric acid (1.96 g, 1.07 mL, 19.2 mmol) was added to the reaction mixture and it was refluxed for 20 h. After completion of the reaction it was quenched with saturated aqueous solution of NaHCO$_3$ (25 mL) and evaporated. The residue was dissolved in chloroform (300 mL) and washed with water (3×75 mL) and brine (2×75 mL), dried over magnesium sulphate and evaporated. The crude product was purified by flash column chromatography (n-Heptane-Ethyl acetate; 20:1) gave 25.50 g (72.30%) of the title compound (11a) as a colorless liquid. GC-MS: >98.1% MS (EI): 184.

Ethyl dec-9-enoate (11b)

Decenoic acid (12) (30.60 g, 180 mmol) was dissolved in dry methanol (300 mL) and 0.1 equivalent of sulfuric acid (1.84 g, 0.99 mL, 18 mmol) was added to the reaction mixture and it was refluxed for 20 h. After completion of the reaction it was quenched with saturated aqueous solution of NaHCO$_3$ (25 mL) and evaporated. The residue was dissolved in chloroform (300 mL) and washed with water (3×75 mL) and brine (2×75 mL), dried over magnesium sulphate and evaporated. The crude product was purified by flash column chromatography (n-Heptane-Ethyl acetate; 20:1) to yield 23.50 g (65.90%) of the title compound (11b) as a colorless liquid. GC-MS: >98.5% MS (EI): 198.

Propan-2-yl dec-9-enoate (11c)

Decenoic acid (12) (15.00 g, 88.1 mmol) was dissolved in dry 2-propanol (200 mL) and 0.1 equiv. of sulfuric acid (0.9 g, 0.49 mL, 8.81 mmol) was added to the reaction mixture and it was refluxed for 20 h. After completion of the reaction it was quenched with saturated aqueous solution of NaHCO$_3$ (25 mL) and evaporated. The residue was dissolved in chloroform (300 mL) and washed with water (3×75 mL) and brine (2×75 mL), dried over magnesium sulphate and evaporated. The crude product was purified by distillation (98-

104° C./8 Hg mm) to yield 14.56 g (77.80%) of the title compound (11c) as a colorless liquid. GC-MS: >99.0% MS (EI): 212.

Cross metathesis of oct-7-enol and 3-methylhex-5-enol derivatives

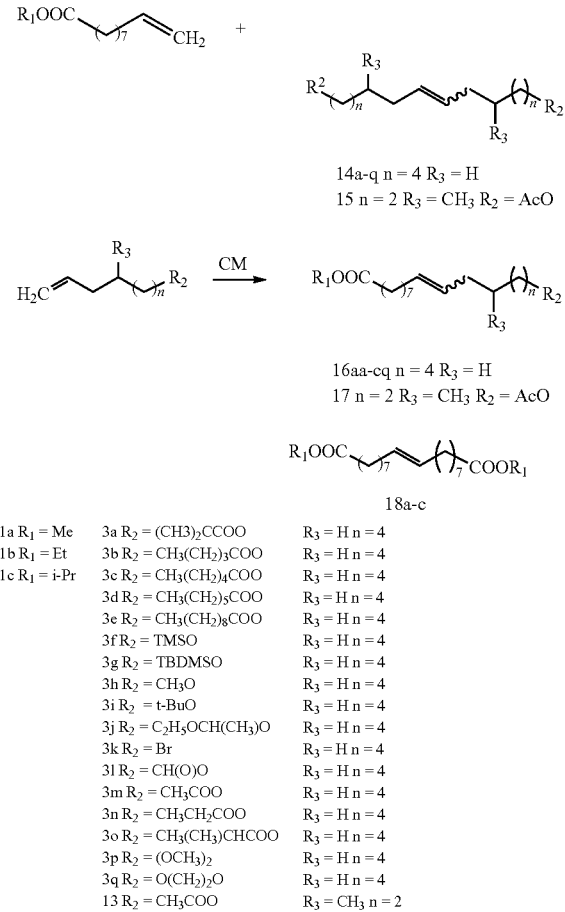

Scheme 2. Cross methathesis of decenoic acid esters (11a-c) with oct-7-enol and 3-methylhex-5-enol (3a-q and 13).

14a-q n = 4 $R_3$ = H
15 n = 2 $R_3$ = $CH_3$ $R_2$ = AcO

16aa-cq n = 4 $R_3$ = H
17 n = 2 $R_3$ = $CH_3$ $R_2$ = AcO 18a-c

| 11a $R_1$ = Me | 3a $R_2$ = $(CH3)_2CCOO$ | $R_3$ = H n = 4 |
| 11b $R_1$ = Et | 3b $R_2$ = $CH_3(CH_2)_3COO$ | $R_3$ = H n = 4 |
| 11c $R_1$ = i-Pr | 3c $R_2$ = $CH_3(CH_2)_4COO$ | $R_3$ = H n = 4 |
| | 3d $R_2$ = $CH_3(CH_2)_5COO$ | $R_3$ = H n = 4 |
| | 3e $R_2$ = $CH_3(CH_2)_8COO$ | $R_3$ = H n = 4 |
| | 3f $R_2$ = TMSO | $R_3$ = H n = 4 |
| | 3g $R_2$ = TBDMSO | $R_3$ = H n = 4 |
| | 3h $R_2$ = $CH_3O$ | $R_3$ = H n = 4 |
| | 3i $R_2$ = t-BuO | $R_3$ = H n = 4 |
| | 3j $R_2$ = $C_2H_5OCH(CH_3)O$ | $R_3$ = H n = 4 |
| | 3k $R_2$ = Br | $R_3$ = H n = 4 |
| | 3l $R_2$ = CH(O)O | $R_3$ = H n = 4 |
| | 3m $R_2$ = $CH_3COO$ | $R_3$ = H n = 4 |
| | 3n $R_2$ = $CH_3CH_2COO$ | $R_3$ = H n = 4 |
| | 3o $R_2$ = $CH_3(CH_3)CHCOO$ | $R_3$ = H n = 4 |
| | 3p $R_2$ = $(OCH_3)_2$ | $R_3$ = H n = 4 |
| | 3q $R_2$ = $O(CH_2)_2O$ | $R_3$ = H n = 4 |
| | 13 $R_2$ = $CH_3COO$ | $R_3$ = $CH_3$ n = 2 |

All metathesis reactions were carried out in a nitrogen-filled glovebox in oven dried glassware.

General Procedure of Cross Metathesis Reactions without Trioctylaluminum (Procedure A):

In an open screw cap vial the 0.1 M solution of metathesis catalyst (in dry benzene) (25-1000 ppm) was added to the mixture of decenoate (11a-c) (10.9 mmol) and octenol derivative (3a-q and 13) (10.9 mmol) and the reaction mixture was stirred at rt for 4-20 h, then it was quenched with 0.2 mL diethyl ether (Analysis: ca. 100 µL of the reaction mixture was filtered through a silica pad (ca. 4-5 mL) the pad was washed with a mixture of n-heptane and EtOAc (7:3, 15 mL) and the filtrate was analyzed by GC-MS.).

General Procedure of Cross Metathesis Reactions in the Presence of Trioctylaluminum (Procedure B):

In an open screw cap vial 0.5 mol % of trioctylaluminum was added to the mixture of decenoate (11a-c) (10.9 mmol) and octenol derivative (3a-q and 13) (10.9 mmol) and the reaction mixture was stirred at rt for 1 h, then the 0.1 M solution of metathesis catalyst (in dry benzene) (25-1000 ppm) was also added to the reaction mixture and stirring was continued for 4-20 h, then it was quenched with 0.2 mL diethyl ether (Analysis: ca. 100 µL of the reaction mixture was filtered through a silica pad (ca. 4-5 mL), the pad was washed with the mixture of n-heptane and EtOAc (7:3, 15 mL) and the filtrate was analyzed by GC-MS.).

EXAMPLE 1

In an open screw cap vial the 0.1 M solution of X052 in dry benzene (10.9 µL, 50 ppm) was added to the mixture of purified methyl decenoate (11a) (2.00 g, 10.9 mmol, 2.28 mL) and purified tert-butyl ether (3i) (2.00 g, 10.9 mmol, 2.52 mL) and the reaction mixture was stirred at rt for 20 h, then it was quenched with 0.2 mL of diethyl ether (Analysis: ca. 100 µL of reaction mixture was filtered through silica pad (ca. 4-5 mL) and washed with the mixture of n-heptane and EtOAc (7:3, 15 mL) and the filtrate was analyzed by GC-MS.). The CM reaction of 11a with 3i afforded a statistical mixture of 14i, 16ai and 18a (1:2:1) with 95% conversion for both starting olefins and E/Z ratios were found to be 85/15 for all three compounds.

EXAMPLE 2

In an open screw cap vial 0.5 mol % of trioctylaluminum (25 w % in hexane) (80 mg, 5.45*$10^{-2}$ mmol, 114 µL) was added to the mixture of methyl decenoate (11a) (2.00 g, 10.9 mmol, 2.28 mL) and tert-butyl ether (3i) (2.00 g, 10.9 mmol, 2.52 mL) and the reaction mixture was stirred at rt for 1 h, then the 0.1 M solution of X190 in dry benzene (5.45 µL, 25 ppm) was also added to the reaction mixture and stirring was continued for 20 h, then it was quenched with 0.2 mL of diethyl ether (Analysis: ca. 100 µL of the reaction mixture was filtered through silica pad (ca. 4-5 mL) and washed with the mixture of n-heptane and EtOAc (7:3, 15 mL) and the filtrate was analyzed by GC-MS.). The CM reaction of 11a with 3i afforded a statistical mixture of 14i, 16ai and 18a (1:2:1) with 95% conversion for both starting olefins and E/Z ratios were found to be 84/16 for all three compounds.

EXAMPLE 3

Methyl decenoate (11a) (51.2 g, 278 mmol, 58.0 mL) and tert-butyl octenyl ether (3i) (50.4 g, 273 mmol, 63.0 mL) were charged in a 500 mL round-bottom flask and the mixture was stirred for ten minutes, then 0.1 M solution of X039 in dry benzene (560 µL, 100 ppm) was added in one portion. The reaction vessel was connected to a vacuum pump and the reaction mixture was stirred at room temperature under 50 mbar dynamic vacuum for 4 hours. GC-MS analysis of the crude product found 90% conversion for both starting olefins. Non-anhydrous ethyl acetate (10 mL) was added to the reaction mixture to quench the metathesis reaction. The quenched mixture was passed through a pad of silica (approx. 20 mL) using 500 mL ethyl acetate as eluent. Volatiles were removed in vacuo to afford the crude product as a practically colourless oil (92.4 g). Metathesis products 14i, 16ai and 18a were formed in the statistical (1:2:1) ratio and E/Z ratios were found to be 9/91 for all three compounds.

EXAMPLE 4

Methyl decenoate (11a) (0.675 g, 3.66 mmol, 765 µL) and octenyl acetate (3m) (0.623 g, 3.66 mmol, 700 µL) were charged in a 30 mL glass vial and the mixture was homogenized, then 0.1 M solution of X054 in dry benzene (74 μL, 1000 ppm) was added in one portion. The vial was connected to a vacuum pump and the reaction mixture was stirred under 50 mbar dynamic vacuum at room temperature for 6 hours (90% conversion for both starting olefins according to GC-MS). Non-anhydrous diethyl ether (10 mL) was added to it to quench the metathesis reaction. The mixture was passed through a silica pad (10 mL) using n-Heptane-Ethyl acetate; 1:1 solvent mixture as eluent. Approximately 75 mL filtrate was collected. Solvent was removed in vacuo to afford the metathesis product mixture as a slightly brownish oil (1.18 g). Metathesis products 14m, 16am and 18a were formed in the statistical (1:2:1) ratio and E/Z ratios were found to be 11/89 for all three compounds.

EXAMPLE 5

Methyl decenoate (11a) (21.4 mg, 0.116 mmol, 24.2 μL) and octenyl acetate (3m) (19.6 mg, 0.115 mmol, 22.0 μL) were charged in a 4 mL glass vial and the mixture was homogenized, then 0.1 M solution of X038 in dry benzene (11.5 μL, 5000 ppm) was added in one portion. The vial was closed with a pierced cap and the reaction mixture was stirred under atmospheric pressure at room temperature. (Analysis: 20 μL of the reaction mixture was mixed with 200 μL of non-anhydrous diethyl ether within the glovebox to quench the metathesis reaction, then the quenched sample was passed through a silica plug (approx. 2 cm thick layer in a Pasteur-pipette) using 4 mL n-Heptane-Ethyl acetate; 1:1 solvent mixture as eluent and the filtrate was analyzed by GC-MS. Sample taken after 2 hours showed 57% conversion for both starting olefins (11a, 3m) and cross metathesis products 14m, 16am and 18a were formed in the statistical (1:2:1) ratio. E/Z ratios were found to equal to 3/97 for all three cross metathesis products. A sample was taken after 2.5 days to find only 68% conversion of both starting olefins and E/Z=4/96 ratios for all three metathesis products.

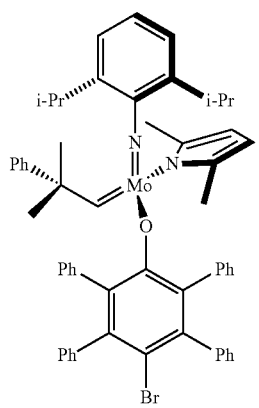

X052

N-[4-bromo-2,3,5,6-tetraphenylphenoxy(2,5-dimethyl-1H-pyrrol-1-yl)(2-methyl-2-phenylpropylidene)molybdenumylidene]-2,6-bis(propan-2-yl)aniline -continued

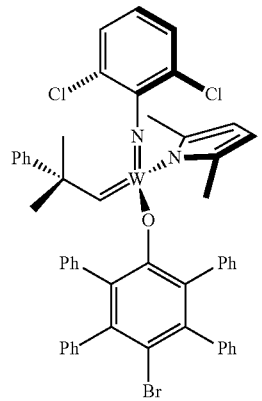

X190

N-[4-bromo-2,3,5,6-tetraphenylphenoxy(2,5-dimethyl-1H-pyrrol-1-yl)(2-methyl-2-phenylpropylidene)tungstenylidene]-2,6-dichloroaniline

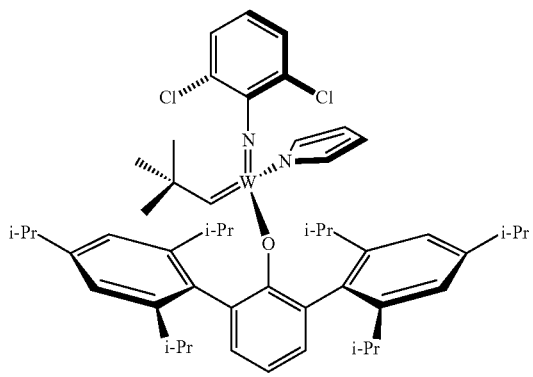

X038

N-{2,6-bis[2,4,6-tris(propan-2-yl)phenyl]phenoxy(2,2-dimethylpropylidene)1H-pyrrol-1-yltungstenylidene}-2,6-dichloroanilene

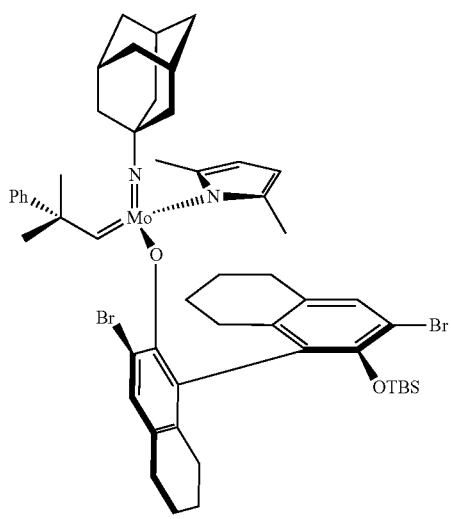

X039

N-{[(3-bromo-1-{3-bromo-2-[(tert-butyldimethylsilyl)oxy]-5,6,7,8-tetrahydronaphthalen-1-yl}-5,6,7,8-tetrahydronaphthalen-2-yl)oxy](2,5-dimethyl-1H-pyrrol-1-yl)(2-methyl-2-phenylpropylidene)molybdenumylidene}adamantan-1-amine -continued

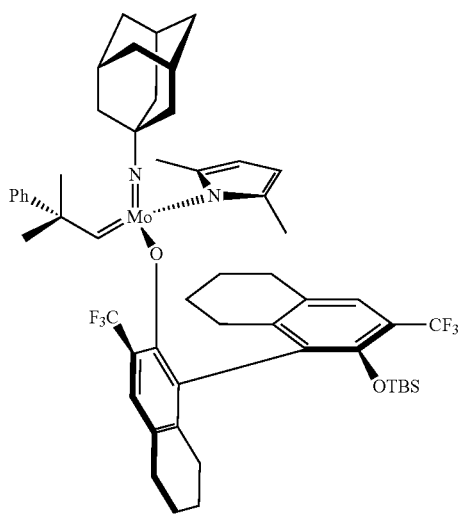

X054

N-{[(1-{2-[(tert-butyldimethylsilyl)oxy]-3-(trifluoromethyl)-5,6,7,8-tetrahydronaphthalen-1-yl}-3-(trifluoromethyl)-5,6,7,8-tetrahydronaphthalen-2-yl)oxy](2,5-dimethyl-1H-pyrrol-1-yl)(2-methyl-2-phenylpropylidene)molybdenumylidene}adamantan-1-amine

EXAMPLE 6

In an open screw cap vial the 0.1 M solution of X190 in dry benzene (26.2 μL, 400 ppm) was added to the mixture of purified methyl decenoate (11a) (600 mg, 3.27 mmol, 683 μL) and purified carbonate (3l) (609 mg, 3.27 mmol) and the reaction mixture was stirred at rt for 20 h, then it was quenched with 0.2 mL of diethyl ether (Analysis: ca. 100 μL of reaction mixture was dissolved in methanol (1 mL) and a small amount sodium methoxide was added to the solution and it was stirred at rt for 4 h. After that it was diluted with water (0.5 mL) and extracted with dichloromethane (2×2 mL), dried over magnesium sulphate and evaporated. The sample was analyzed by GC-MS.). The CM reaction of 11a with 3l afforded a statistical mixture of 14l, 16al and 18a (1:2:1) with 95% conversion.

EXAMPLE 7

In an open screw cap vial 0.5 mol % of trioctylaluminum (25 w % in hexane) (40 mg, 2.72*10$^{-2}$ mmol, 57 μL) was added to the mixture of methyl decenoate (11a) (1.00 g, 5.43 mmol, 1.13 mL) and carbonate (3l) (1.00 g, 5.43 mmol) and the reaction mixture was stirred at rt for 1 h, then the 0.1 M solution of X190 in dry benzene (21.7 μL, 200 ppm) was also added to the reaction mixture and stirring was continued for 20 h, then it was quenched with 0.2 mL of diethyl ether (Analysis: ca. 100 μL of reaction mixture was dissolved in methanol (1 mL) and a small amount sodium methoxide was added to the solution and it was stirred at rt for 4 h. After that it was diluted with water (0.5 mL) and extracted with dichloromethane (2×2 mL), dried over magnesium sulphate and evaporated. The sample was analyzed by GC-MS.). The CM reaction of 11a with 3l afforded a statistical mixture of 14l, 16al and 18a (1:2:1) with 35% conversion.

EXAMPLE 8

Methyl decenoate (11a) (0.098 g, 0.50 mmol, 104 μL) and 3-methylhex-5-enyl acetate (13) (0.078 g, 0.50 mmol, 85 μL) were measured into a 4 mL vial, 0.1 M solution of X054 in dry benzene (5.0 μL, 500 ppm) was added in one portion, then the vial was connected to a vacuum pump and the reaction was stirred at room temperature under 50 mbar dynamic vacuum. (Analysis: 5.0 μL of the reaction mixture was mixed with 200 μL non-anhydrous diethyl ether to quench the metathesis reaction, then the quenched sample was passed through a silica plug (approx. 2 cm thick layer in a Pasteur-pipette) using 4 mL n-Heptane-Ethyl acetate; 1:1 solvent and the filtrate was analyzed by GC-MS. Sample taken after 19 hours showed 97% conversion for both starting olefins (11a, 13) and cross metathesis products 15, 17 and 18a were formed in the statistical (1:2:1) ratio. Since E- and Z-isomers of the acetate compound 17 separate less readily in GC-MS than isomers of deprotected alcohol 22, the acetate moiety was selectively cleaved via trans-esterification of 20 μL reaction mixture samples with dry methanol/NaOMe (1.0 mL methanol, approx. 5 mg NaOMe) following a protocol analogous to that described in Example 9. The resulting material was analyzed by GC-MS to determine E/Z ratio of compound 17. It was found that the more branched the chain is (2, 1 or no methyl groups in homoallylic position(s) of the double bond, the higher the Z-selectivity is. E/Z ratios for cross metathesis products: 15 (2/98); 17 (5/95); 18a (7/93). A sample taken only after 4 hours showed 89% conversion for 13 and 95% conversion 11a, indicating that the more branched substrate undergoes metathesis less readily. E/Z ratios were the same as those reported for the sample taken after 19 hours.

EXAMPLE 9

The experiment described in Example 8 was repeated using catalyst X039. In this case 96% conversion of both starting olefins was achieved within 4 hours. Cross metathesis products 15, 17 and 18a were again formed in the statistical (1:2:1) ratio. E/Z ratios: 15 (2/98); 17 (7/93); 18a (12/88).

EXAMPLE 10

Cleavage of a tBu-Ether Protecting Group

Crude product obtained in Example 3 was charged in a 500 mL two-necked round-bottom flask and dissolved in dry dichloromethane (200 mL, freshly distilled from CaH$_2$). The flask was flushed with nitrogen and cooled to 0° C. by applying an ice/water bath. Titanium tetrachloride was added in small portions over 15 minutes and the mixture was stirred for additional 15 minutes. Still at 0° C., under constant cooling, saturated aqueous solution of NH$_4$Cl solution (20 mL) was added dropwise. The mixture was allowed to warm to room temperature and brine was added to ease phase separation (1×100 mL). Phases were separated and the organic phase was washed with brine (2×50 mL) and dried over MgSO$_4$. Volatiles were removed in vacuo. Column chromatographic purification of the resulting oil using silica and n-heptane-diethyl ether; 2:1 as eluent afforded the desired product (21a) as a colorless oil (31.0 g, 109 mmol, 79% overall yield for the cross metathesis and tert-butyl cleavage steps). The E/Z isomer ratio was invariably 9/91.

Synthesis of Ambrettolide Intermediate ω-Hydroxy Esters (21a-c, 22) Via Selective Alcohol Deprotection:

rate 4° C./min to 260° C., hold time 0 min, ramp rate 40° C./min to 340° C., hold time 3.2 min carrier gas nitrogen.

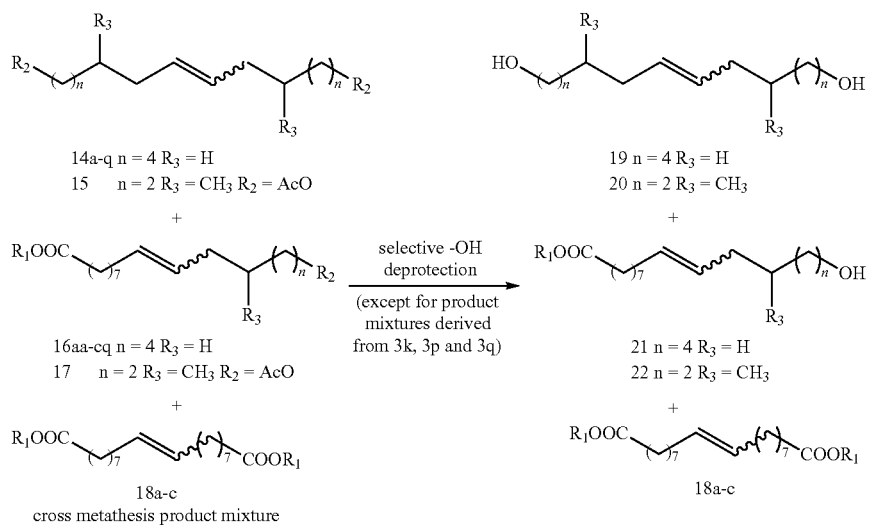

Scheme 4. Synthesis of ω-hydroxy esters (21a-c, 22).

EXAMPLE 11

Cleavage of an Ester Protecting Group

The crude product obtained in Example 4 was dissolved in 3 mL dry methanol, 20 mg sodium methylate was added and the mixture was stirred at room temperature for 2 hours. The mixture was passed through a silica pad (7 mL silica) and the pad was washed with ethyl acetate (75 mL). The filtrate was evaporated to afford 1013 mg crude transesterification product. The desired product was isolated by flash column chromatography using n-heptane-diethyl ether; 2:1. The desired product (21a, $R_1$=Me) was obtained as a yellowish oil (355 mg, 1.25 mmol, 68% overall yield for the cross metathesis and acetate cleavages). The E/Z isomer ratio was invariably 11/89.

GC-MS Analytical Method for Product Identification (Method A):

GC analyses were run using a flame ionization detector (FID). Column: ZB-35HT Inferno (35% Phenyl 65% Dimethylpolysiloxane) from Phenomenex; 30 m×0.25 mm (i.d.)×0.25 mm film thickness. GC and column conditions: injector temperature 370° C.; detector temperature 240° C.; oven temperature, starting temperature 50° C., hold time 5 min, ramp rate 25° C./min to 340° C., hold time 12 min; carrier gas nitrogen.

GC-MS Analytical Method for Product Identification (Method B):

GC analyses were run using a flame ionization detector (FID). Column: ZB-35HT Inferno (35% Phenyl 65% Dimethylpolysiloxane) from Phenomenex; 30 m×0.25 mm (i.d.)×0.25 mm film thickness. GC and column conditions: injector temperature 370° C.; detector temperature 240° C.; oven temperature, starting temperature 55° C., hold time 2 min, ramp rate 25° C./min to 200° C., hold time 0 min; ramp

TABLE 1

Cross metathesis of decenoic acid esters and protected oct-7-enol derivatives.

| Entry | Substrates | Catalyst | Loading (ppm (mol)) | Conversion | E/Z ratio | Procedure |
|---|---|---|---|---|---|---|
| 1 | 11a and 3m | X007 | 2000 ppm | 80% | 82/18 | A |
| 2 | 11a and 3m | X007 | 1000 ppm | 15% | 80/20 | A |
| 3 | 11a and 3m | X008 | 2000 ppm | 25% | 81/19 | A |
| 4 | 11a and 3m | X001 | 2500 ppm | 85% | 85/15 | A |
| 5 | 11a and 3m | X030 | 2000 ppm | 50% | 83/17 | A |
| 6 | 11a and 3m | X041 | 2000 ppm | 50% | 83/17 | A |
| 7 | 11a and 3m | X042 | 2000 ppm | 90% | 84/16 | A |
| 8 | 11a and 3m | X046 | 2000 ppm | 90% | 81/19 | A |
| 9 | 11a and 3m | X040 | 2000 ppm | 95% | 85/15 | A |
| 10 | 11a and 3m | X042 | 1000 ppm | 80% | 83/17 | A |
| 11 | 11a and 3m | X052 | 1000 ppm | 85% | 84/16 | A |
| 12 | 11a and 3m | X051 | 1000 ppm | 35% | 85/15 | A |
| 13 | 11a and 3m | X004 | 1000 ppm | 60% | 86/14 | A |
| 14 | 11a and 3m | X042 | 500 ppm | 15% | 85/15 | A |
| 15 | 11a and 3m | X123 | 200 ppm | 10% | 85/15 | B |
| 16 | 11a and 3m | X054 | 1000 ppm | 90% | 11/89 | Example 4 |
| 17 | 11a and 3m | X038 | 5000 ppm | 68% | 4/96 | Example 5 |
| 18 | 11a and 3h | X042 | 1000 ppm | 95% | 84/16 | A |
| 19 | 11a and 3h | X052 | 1000 ppm | 95% | 85/15 | A |
| 20 | 11a and 3h | X052 | 250 ppm | 95% | 84/16 | A |
| 21 | 11a and 3h | X042 | 250 ppm | 95% | 85/15 | A |
| 22 | 11a and 3h | X052 | 100 ppm | 95% | 84/16 | A |
| 23 | 11a and 3h | X042 | 100 ppm | 95% | 85/15 | A |
| 24 | 11a and 3h | X052 | 50 ppm | 85% | 85/15 | A |
| 25 | 11a and 3h | X042 | 50 ppm | 40% | 84/16 | A |
| 26 | 11a and 3h | X051 | 50 ppm | 75% | 85/15 | A |
| 27 | 11a and 3h | X061 | 50 ppm | 85% | 84/16 | A |
| 28 | 11a and 3h | X062 | 50 ppm | 65% | 84/16 | A |
| 29 | 11a and 3h | X063 | 50 ppm | 40% | 70/30 | A |
| 30 | 11a and 3g | X052 | 100 ppm | 95% | 84/16 | A |
| 31 | 11a and 3g | X042 | 100 ppm | 70% | 85/15 | A |
| 32 | 11a and 3i | X052 | 100 ppm | 90% | 83/17 | A |
| 33 | 11b and 3i | X052 | 100 ppm | 95% | 85/15 | A |
| 34 | 11c and 3i | X052 | 100 ppm | 95% | 84/16 | A |
| 35 | 11a and 3i | X039 | 100 ppm | 90% | 9/91 | Example 3 |
| 36 | 11a and 3i | X052 | 50 ppm | 90% | 84/16 | A |
| 37 | 11a and 3i | X061 | 50 ppm | 20% | 83/17 | A |
| 38 | 11a and 3i | X059 | 50 ppm | 20% | 84/16 | A |
| 39 | 11a and 3i | X004 | 50 ppm | 20% | 85/15 | A |
| 40 | 11a and 3i | X076 | 50 ppm | 90% | 60/40 | A |

TABLE 1-continued

Cross metathesis of decenoic acid esters and protected oct-7-enol derivatives.

| Entry | Substrates | Catalyst | Loading (ppm (mol)) | Conversion | E/Z ratio | Procedure |
|---|---|---|---|---|---|---|
| 41 | 11a and 3i | X114 | 50 ppm | 15% | 80/20 | A |
| 42 | 11a and 3i | X123 | 50 ppm | 85% | 85/15 | A |
| 43 | 11a and 3i | X123 | 25 ppm | 90% | 85/15 | B |
| 44 | 11a and 3i | X149 | 25 ppm | 10% | 84/16 | B |
| 45 | 11a and 3i | X154 | 25 ppm | 85% | 85/16 | B |
| 46 | 11a and 3i | X123 | 17 ppm | 75% | 84/16 | B |
| 47 | 11a and 3i | X123 | 12 ppm | 55% | 84/16 | B |
| 48 | 11a and 3l | X190 | 400 | 95% | n/a | Example 6 |
| 49 | 11a and 3l | X190 | 200 | 32% | n/a | A |
| 50 | 11a and 3l | X190 | 200 | 35% | n/a | Example 7 |
| 51 | 11a and 3l | X190 | 100 | 10% | n/a | A |

TABLE 2

Cross metathesis of decenoic acid esters and protected oct-7-enol derivatives.

| Entry | Substrates | Catalyst | Loading (ppm (mol)) | Conversion | E/Z ratio | Procedure |
|---|---|---|---|---|---|---|
| 48 | 11a and 3i | X190 | 25 ppm | 85% | 85/15 | B |
| 49 | 11a and 3f | X052 | 50 ppm | 60% | 84/16 | B |
| 50 | 11a and 3f | X123 | 50 ppm | 90% | 85/15 | B |
| 51 | 11a and 3f | X123 | 25 ppm | 80% | 84/16 | B |
| 52 | 11a and 3o | X123 | 50 ppm | 50% | 84/16 | B |
| 53 | 11a and 3n | X123 | 50 ppm | 45% | 85/15 | B |
| 54 | 11a and 3c | X052 | 250 ppm | 50% | 84/16 | A |
| 55 | 11a and 3c | X123 | 250 ppm | 80% | 85/15 | A |
| 56 | 11a and 3d | X052 | 500 ppm | 90% | 84/16 | A |
| 57 | 11a and 3d | X123 | 500 ppm | 90% | 85/15 | A |

TABLE 3

Cross metathesis of methyl dec-9-enoate (11a) and 3-methylhex-5-enyl acetate (13).

| Entry | Substrates | Catalyst | Loading (ppm (mol)) | Conversion | E/Z ratio | Procedure |
|---|---|---|---|---|---|---|
| 1 | 11a and 13 | X054 | 500 ppm | 97% (19 h) | 5/95 | Example 6 |
| 2 | 11a and 13 | X039 | 500 ppm | 96% (4 h) | 7/93 | Example 7 |

TABLE 4

Characterization of cross metathesis products.

| Entry | CM products | GC-MS | Retention | MS (mw) |
|---|---|---|---|---|
| 1 | 16aa | Method A | 15.82 min | 368 [M]$^+$ |
| 2 | 16ab | Method A | 16.44 min | 368 [M]$^+$ |
| 3 | 16ac | Method A | 16.74 min | 382 [M]$^+$ |
| 4 | 16ad | Method A | 17.10 min | 396 [M]$^+$ |
| 5 | 16ae | Method A | 18.25 min | 438 [M]$^+$ |
| 6 | 16af | Method A | 15.02 min | 356 [M]$^+$ |
| 7 | 16ag | Method A | 15.72 min | 399 [M]$^+$ |
| 8 | 16ah | Method A | 14.60 min | 298 [M]$^+$ |
| 9 | 16ai | Method A | 15.31 min | 284 [M-CCH$_3$]$^+$ |
| 10 | 16aj | Method A | 15.52 min | 355 [M]$^+$ |
| 11 | 16ak | Method A | 15.98 min | 346, 348 [M]$^+$ |
| 12[a] | 16al | Method A | 14.98 min | 284 [M]$^+$ |
| 13 | 16an | Method A | 15.43 min | 326 [M]$^+$ |
| 14 | 16ao | Method A | 15.83 min | 340 [M]$^+$ |
| 15 | 16ap | Method A | 15.94 min | 354 [M]$^+$ |
| 16 | 16ar | Method A | 16.03 min | 325 [M]$^+$ |
| 17 | 16bi | Method A | 15.27 min | 355 [M]$^+$ |
| 18 | 16bj | Method A | 15.72 min | 298 [M-CH(CH$_3$)OC$_2$H$_5$]$^+$ |
| 19 | 16bn | Method A | 15.68 min | 340 [M]$^+$ |
| 20 | 16ci | Method A | 15.30 min | 312 [M-CCH$_3$]$^+$ |
| 21 | 16cj | Method A | 15.75 min | 385 [M]$^+$ |
| 22 | 17 | Method B | 15.74 min | 312 [M]$^+$, 252 [M-AcOH]$^+$ |

[a]Before the product identification the protective group was cleaved by sodium methoxide in methanol.

Recycling of Homodimeric Side Product(s) Via Cross Metathesis:

Scheme 5.

Scenario 1:

Scenario 2:

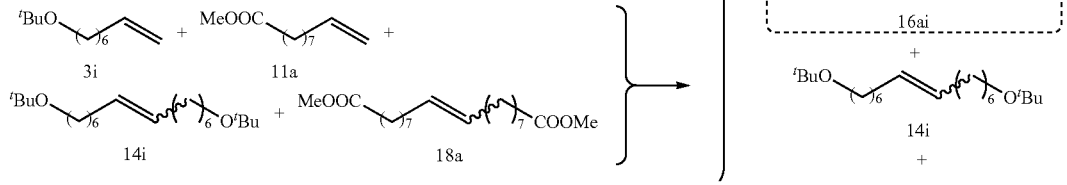

Scenario 3:

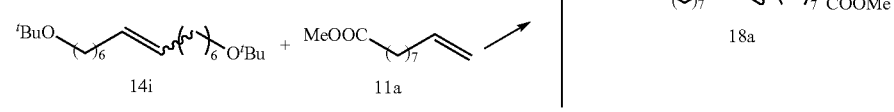

Scenario 4:

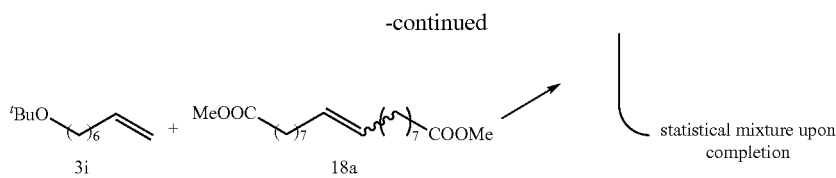

Strategies to recycle homodimeric side products (14i, 18a or both) formed in the cross metathesis of methyl dec-9-enoate (11a) and 8-(tert-butoxy)oct-1-ene(3i).

EXAMPLE 12

(Scenario 1):

The homodimer of tert-butyl octenyl ether (14i) (0.085 g, 0.25 mmol, 100 µL, E/Z=85/15) and the homodimer of methyl dec-9-enoate (18a) (0.086 g, 0.25 mmol, 92 µL, E/Z=85/15) were charged in a 4 mL screw cap vial and the mixture was homogenized. Metathesis catalyst X190, (1.0*10$^{-4}$ mmol, 10 µL, 0.01 M in benzene) was added in one portion. The vial was closed with a septum cap and the reaction mixture was stirred at room temperature overnight. The reaction mixture was subjected to air and mixed with 1 mL non-anhydrous ethyl acetate to quench the reaction. The sample was then passed through a silica pad using pure ethyl acetate as eluent (5 mL) and the filtrate was analyzed by GC-MS. The reaction afforded 14i, 16ai and 18a with 95% recycling efficiency. In case of compound 16ai the ratio of E- and Z-isomers was found to correspond to the thermodynamical equilibrium value (E/Z≈85/15).

EXAMPLE 13

(Scenario 2):

8-(tert-Butoxy)oct-1-ene (3i) (0.092 g, 0.50 mmol, 114 µL) and methyl dec-9-enoate (11a) (0.092 g, 0.50 mmol, 104 µL) along with the homodimer of tert-butyl octenyl ether (14i) (0.086 g, 0.25 mmol, 100 µL, E/Z=85/15) and the homodimer of methyl dec-9-enoate (18a) (0.086 g, 0.25 mmol, 92 µL, E/Z=85/15) were charged in a 4 mL screw cap vial and the mixture was homogenized. Metathesis catalyst X052 (2.0*10$^{-4}$ mmol, 20 µL, 0.01 M in benzene) was added in one portion. The vial was closed with a pierced cap and the reaction mixture was stirred at room temperature. Samples (10 µL) taken from the reaction mixture after 2 h and 18 h reaction times were subjected to air and mixed with 0.2 mL non-anhydrous diethyl ether to quench the reaction. The samples were then passed through a silica pad using pure EtOAc as eluent (5 mL) and the filtrate was analyzed by GC-MS. For the sample taken at 2 hours reaction time GC-MS analysis found 90% recycling efficiency and in case of compound 16ai the ratio of E- and Z-isomers was found to correspond to the thermodynamical equilibrium value (E/Z≈85/15). The sample taken after 18 hours showed identical values regarding both recycling efficiency and E/Z ratio.

EXAMPLE 14

(Scenario 3):

Methyl dec-9-enoate (11a) (0.184 g, 1.0 mmol, 208 µL) and the homodimer of tert-butyl octenyl ether (14i) (0.170 g, 0.5 mmol, 200 µL, E/Z=85/15) were charged in a 4 mL screw cap vial along with trioctylaluminum (4.0*10$^{-4}$ mmol, 16.8 µL, 0.024 M in benzene) and the mixture was stirred at room temperature for 3.5 hours, then metathesis catalyst X190 (4.0*10$^{-4}$ mmol, 40 µL, 0.01 M in benzene) was added in one portion. The vial was closed tightly and the reaction mixture was stirred at room temperature for 1.5 hours. The vial was connected to a 50 mbar dynamic vacuum source and its content was stirred for further 2.5 hours. The reaction mixture was subjected to air and mixed with 1 mL non-anhydrous ethyl acetate to quench the reaction. The sample was then passed through a silica pad using pure ethyl acetate as eluent (5 mL) and the filtrate was analyzed by GC-MS. GC-MS analysis found 95% recycling efficiency and in case of compound 16ai the ratio of E- and Z-isomers was found to correspond to the thermodynamical equilibrium value (E/Z≈85/15).

EXAMPLE 15

(Scenario 4):

8-(tert-Butoxy)oct-1-ene (3i) (0.186 g, 1.0 mmol, 235 µL) and the homodimeric olefin (18a) (0.170 g, 0.5 mmol, 183 µL, E/Z=85/15) were charged in a 4 mL screw cap vial along with trioctylaluminum (2.0*10$^{-4}$ mmol, 8.4 µL, 0.024 M in benzene) and the mixture was stirred at ca. 30° C. for 3.5 hours, then metathesis catalyst X190 (2.0*10$^{-4}$ mmol, 20 µL, 0.01 M in benzene) was added in one portion. The vial was closed tightly and the reaction mixture was stirred at ca. 30° C. for 1.0 hours. The vial was connected to a 50 mbar dynamic vacuum source and its content was stirred for further 1.5 hours. The reaction mixture was subjected to air and mixed with 1 mL non-anhydrous ethyl acetate to quench the reaction. The sample was then passed through a silica pad using pure ethyl acetate as eluent (5 mL) and the filtrate was analyzed by GC-MS. GC-MS analysis found 95% recycling efficiency and in case of compound 16ai the ratio of E- and Z-isomers was found to correspond to the thermodynamical equilibrium value (E/Z≈85/15).

TABLE 5

Selected examples of recycling experiments based on various strategies outlined in Scheme 5.

| Entry | Substrates, molar ratios | Catalyst | Loading (ppm (mol)) in monomer equivalents[a] | Recycling efficiency %[b] | E/Z ratio (16ai) | Procedure |
|---|---|---|---|---|---|---|
| 1 | 14i, 18a | X190 | 100 ppm | 95% | 85/15 | Example 10 |
| 2 | 1:1 | X052 | 100 ppm | 40% | 85/15 | Conditions of Example 10 |

TABLE 5-continued

Selected examples of recycling experiments based on various strategies outlined in Scheme 5.

| Entry | Substrates, molar ratios | Catalyst | Loading (ppm (mol)) in monomer equivalents[a] | Recycling efficiency %[b] | E/Z ratio (16ai) | Procedure |
|---|---|---|---|---|---|---|
| 3 | 3i, 11a, 14i, 18a | X052 | 100 ppm | 90% | 85/15 | Example 11 |
| 4 | 2:2:1:1 | X190 | 100 ppm | 70% | 85/15 | Conditions of Example 11 |
| 5 | 11a, 14i 2:1 | X190 | 200 ppm | 95% | 85/15 | Example 12 |
| 6 | 3i, 18a 2:1 | X190 | 100 ppm | 95% | 85/15 | Example 13 |

[a]Monomeric olefins (3i, 11a) equal to 1, while homodimeric olefins (14i, 18a) equal to 2 equivalents of monomeric units. Loadings are given with respect to the sum of all olefinic starting materials.
[b]Recycling efficiency is calculated in the following way: rec. efficiency % = [n(octenyl units in 16ai)/Σn(octenyl units in any form) + n(octenyl units in 16ai)/Σn(octenyl units in any form)] * 100. Its value is 0% for all starting mixtures and equals to 100% for a statistical mixture of 14i, 16ai, 18a.

Experimental Details on the Recycling of Homodimeric Side Product(s) Via Ethenolysis was washed with a mixture of n-heptane and EtOAc (7:3, 15 mL) and the filtrate was analyzed by GC-MS.).

Scheme 6.

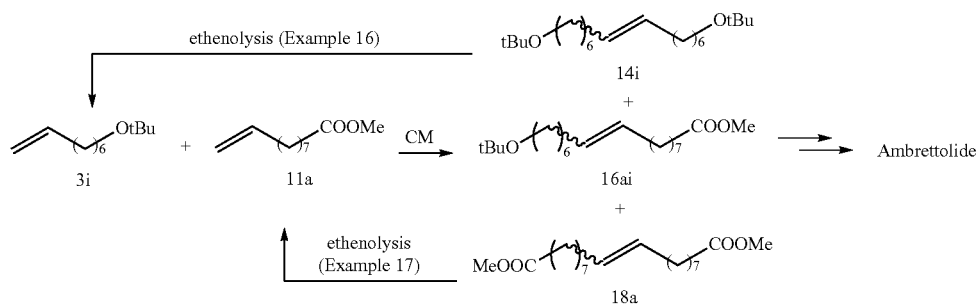

Cross metathesis of tert-butyl octenyl ether (3i) and methyl decenoate (11a) and recycling of by-products (14i and 18a).

TABLE 6

Ethenolysis of tert-butyl ether dimer (14i).[a]

| Entry | Substrate | Catalyst | Loading (ppm (mol)) | Conversion |
|---|---|---|---|---|
| 1 | 14i | X041 | 400 ppm | 65% |
| 2 | 14i | X042 | 400 ppm | 60% |
| 3 | 14i | X052 | 400 ppm | 75% |
| 4 | 14i | X076 | 400 ppm | 60% |
| 5 | 14i | X041 | 200 ppm | 57% |
| 6 | 14i | X042 | 200 ppm | 41% |
| 7 | 14i | X052 | 200 ppm | 52% |
| 8 | 14i | X076 | 200 ppm | 33% |
| 9[b] | 14i | X041 | 200 ppm | 91% |
| 10[b] | 14i | X052 | 200 ppm | 62% |

[a]All reactions were carried out at 0.73 mmol scale, reaction mixtures were stirred at room temperature for 16 h under 11.5 bar ethylene pressure.
[b]n-Heptane was used as solvent to increase the solubility of ethylene.

EXAMPLE 16

General Procedure of Ethenolysis (for Results in Table 6.):

In an open screw cap vial the 0.1 M solution of metathesis catalyst (in dry benzene) (200-400 ppm) was added to 14i or 18a (0.73 mmol) and the reaction mixture was stirred at rt under 11.5 bar ethylene for 20 h, then it was quenched with 0.2 mL diethyl ether (Analysis: ca. 100 μL of the reaction mixture was filtered through a silica pad (ca. 4-5 mL) the pad

TABLE 7

Results of ethenolysis experiments.

| Entry | Substrate | Catalyst | Loading (ppm (mol))[a] | Conditions | Conversion %[b] |
|---|---|---|---|---|---|
| 1 | 14i | X061 | 1000 ppm | Example 16 | 80% (isolated) |
| 2[c] | | X008 | 400 ppm | 4x volume of pentane, r.t., 11.5 bar, 12 h | 80% |
| 3[c] | | | 200 ppm | | 50% |
| 4 | 18a | X008 | 1000 ppm | Example 17 | 86% (isolated) |
| 5[c] | | | 400 ppm | 4x volume of pentane, r.t., 11.5 bar, 12 h | 50% |
| 6[c] | | | 400 ppm | 4x volume of pentane, 2.5 mol % Et₃Al, r.t. 1.5 h then catalyst X008, r.t., 11.5 bar, 12 h | 55% |
| 7[c] | | | 200 ppm | | 30% |

[a]Catalyst loadings given with respect to starting homodimers (14i and 18a).
[b]GC conversions unless indicated otherwise.
[c]Reactions were carried out on 0.5 mmol scale. Work-up analogous to that described for experiments listed in Table 6.

EXAMPLE 17

Diether (14i) (2.47 g; 7.25 mmol) was dissolved in 12.0 mL pentane in a 30 mL oven-dried glass vial equipped with a stir bar, stock solution of catalyst X061 (0.1 M in benzene; 72.6 μL; 0.1 mol %) was added to the reaction mixture and the vial was placed into an autoclave (250 mL inner volume). The autoclave was closed and pressurized to 11.5 bar for 30 minutes. Ethylene source was disconnected and the autoclave was chambered out from the glovebox. The reaction mixture was allowed to stir at room temperature for 12 hours. Ethylene was carefully released, the autoclave lid was removed and 1 mL heptane:EtOAc (non-anhydrous solvents) 1:1 solvent mixture was added subsequently to quench the reaction. The quenched reaction mixture was passed through a silica plug (ca. 10 cm silica layer in a 20 mL syringe barrel) using 150 mL heptane:EtOAc 1:1 solvent mixture as eluent. The filtrate was concentrated in vacuo and the oily residue was distilled bulb-to-bulb ($3.0$-$3.3 \times 10^{-2}$ mbar; 52-55° C.) to afford recovered tert-butyl octenyl ether (3i) as a colorless oil (2.13 g; 11.56 mmol; yield: 80%).

EXAMPLE 18

Procedure and workup were identical to those describe in Example A but catalyst X008 was used. Diester (18a) (2.27 g; 6.67 mmol) dissolved in 9.6 mL n-pentane was ethenolyzed in the presence of catalyst X008 (0.1 M in benzene; 66.4 μL; 0.1 mol %). Bulb-to-bulb distillation ($8.5$-$9.0 \times 10^{-2}$ mbar; 60-61° C.) afforded the title compound as a colorless oil (2.10 g; 11.40 mmol; yield: 86%).

$^1$H-NMR analysis of the crude products before bulb-to-bulb distillation—both for Example 16 and Example 17—showed that crude products consisted of ca. 95% monomer (3i; 11a) and residues of unreacted homodimer (14i; 18a). No signs of undesired side reactions during the ethenolysis or workup were observed. NMR spectra of bulb-to-bulb distilled materials correspond to those of pure 3i and 11a.

The invention claimed is:

1. A method of forming a macrocyclic musk compound comprising the steps of:
   i) cross-metathesizing a first olefin and a second olefin in the presence of a homogeneous transition metal catalyst comprising an alkylidene ligand, to form a statistical mixture of a hetero-dimer intermediate of said first and second terminal olefin, and homo-dimers
   ii) separating the hetero-dimer from the statistical mixture of hetero- and homo-dimers
   iii) and cyclizing the hetero-dimer intermediate to form the macrocyclic musk compound,
   wherein,
   both the first and the second olefins are olefins with a terminal double bond; and
   the second olefin has the formula (II)

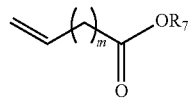

wherein $R_7$ is a branched or non-branched alkyl moiety having 1 to 5 carbon atoms and m is an integer from 1 to 10.

2. A method according to claim 1 wherein the first olefin has the formula (I)

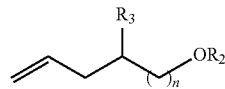

wherein:
   $OR_2$ is a protected hydroxyl group, which is selected from: an alkyl ether group, an ester group, a silyl ether group, and a carbonate group;
   $R^3$ is H or methyl; and,
   n is an integer from 1-8.

3. A method according to claim 1, wherein the hetero-dimer has the formula

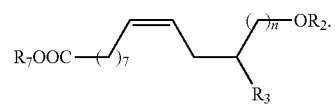

4. A method according to claim 1, wherein the hetero-dimer has the formula

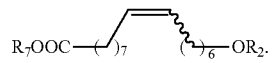

5. A method according to claim 1, wherein the hetero-dimer has the formula

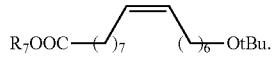

6. A method according to claim 1, wherein the first olefin and second olefin are reacted in a 1:x molar ratio to produce a ratio of hetero-dimer:first homo-dimer:second homo-dimer of $2x:1:1x^2$, where X is an integer or a number having a fractional part, which is greater than 1.

7. A method according to claim 1, wherein the hetero-dimer is formed in admixture with a protected alcohol homo-dimer and a carboxylic acid ester homo-dimer.

8. A method according to claim 7, wherein the mixture of the hetero-dimer, the protected alcohol homo-dimer and the carboxylic acid homo-dimer is formed in a respective molar ratio of 2:1:1.

9. A method according to claim 1, wherein the hetero-dimer is separated from the homo-dimers by distillation at a temperature of 100 to 220 degrees centigrade and a pressure of 1 to 10 mbar.

10. A method according to claim 1, wherein the homo-dimers are recycled by metathesis with ethylene to regenerate the first and second olefins.

11. A method according to claim 10 wherein the homo-dimers are treated with ethylene gas at a pressure of 1 bar to 20 bar.

12. A method according to claim 1, wherein the hetero-dimer is cyclized by trans-esterification.

13. A method according to claim 12 wherein, if the hetero-dimer contains a protected alcohol group, it is first de-protected by hydrolysis before being subjected to cyclization by trans-esterification.

14. A method of forming E/Z 9-ambrettolide according to the method according to claim 1.

15. A method of forming E/Z 9-ambrettolide according to claim 14, wherein the E/Z ratio is from 80:20 to 90:10.

16. A method according to claim 15 wherein the E/Z ratio is 85:15.

17. A method according to claim 1, wherein the catalyst is a molybdenum or tungsten catalyst containing an alkylidene ligand.

18. A method according to claim 1, wherein the catalyst is a compound according to the formula:

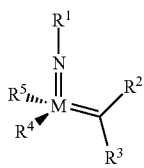

wherein
M=Mo or W; $R^1$ is aryl, heteroaryl, alkyl, or heteroalkyl; which may be substituted;
$R^2$ and $R^3$ can be the same or different and each is hydrogen, alkyl, alkenyl, heteroalkyl, heteroalkenyl, aryl, or heteroaryl; which may be substituted;
$R^5$ is alkyl, alkoxy, heteroalkyl, aryl, aryloxy, heteroaryl, silylalkyl, silyloxy, which may be substituted; and
$R^4$ is a residue $R^6$—X—, wherein
X=O and $R^6$ is aryl, which may be substituted; or
X=S and $R^6$ is aryl, which may be substituted; or
X=O and $R^6$ is ($R^7$, $R^8$, $R^9$)Si; wherein $R^7$, $R^8$, $R^9$ are alkyl or phenyl, which may be substituted; or
X=O and $R^6$ is ($R^{10}$, $R^{11}$, $R^{12}$)C, wherein $R^{10}$, $R^{11}$, $R^{12}$ are independently selected from phenyl, alkyl; which may be substituted;

or,
$R^4$ and $R^5$ are linked together and are bound to M via oxygen.

19. A hetero-dimer having the formula:

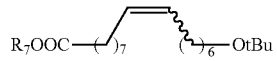

wherein $R_7$ is a branched or non-branched alkyl moiety having 1 to 5 carbon atoms.

20. A hetero-dimer having the formula:

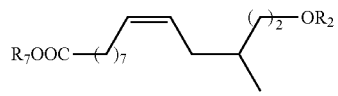

wherein $OR_2$ is a protected hydroxyl group and $R_7$ is a branched or non-branched alkyl moiety having 1 to 5 carbon atoms.

21. The hetero-dimer according to claim 20 having the formula:

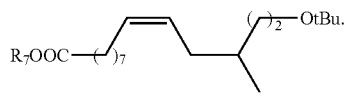

22. A method according to claim 1, wherein:
$R^7$ is methyl or ethyl.

23. A method according to claim 1, wherein:
m is 7.

* * * * *